United States Patent
Mino et al.

(10) Patent No.: US 11,134,836 B2
(45) Date of Patent: Oct. 5, 2021

(54) OPHTHALMOLOGIC INFORMATION PROCESSING APPARATUS, OPHTHALMOLOGIC APPARATUS AND OPHTHALMOLOGIC INFORMATION PROCESSING METHOD

(71) Applicant: TOPCON CORPORATION, Tokyo (JP)

(72) Inventors: Toshihiro Mino, Saitama (JP); Jonathan Liu, Tokyo (JP)

(73) Assignee: TOPCON CORPORATION, Tokyo (JP)

(*) Notice: Subject to any disclaimer, the term of this patent is extended or adjusted under 35 U.S.C. 154(b) by 272 days.

(21) Appl. No.: 16/412,433

(22) Filed: May 15, 2019

(65) Prior Publication Data
US 2020/0221948 A1 Jul. 16, 2020

Related U.S. Application Data

(60) Provisional application No. 62/793,044, filed on Jan. 16, 2019.

(51) Int. Cl.
*A61B 3/00* (2006.01)
*A61B 3/10* (2006.01)
(Continued)

(52) U.S. Cl.
CPC .......... *A61B 3/0025* (2013.01); *A61B 3/0075* (2013.01); *A61B 3/102* (2013.01);
(Continued)

(58) Field of Classification Search
CPC .......... A61B 3/102; A61B 3/103–1035; A61B 3/12
See application file for complete search history.

(56) References Cited

U.S. PATENT DOCUMENTS

8,085,408 B2 * 12/2011 Everett .............. G01B 9/02091
356/497
8,442,286 B2 * 5/2013 Imamura .............. A61B 5/0066
382/128
(Continued)

FOREIGN PATENT DOCUMENTS

EP 2 404 545 A2 1/2012
EP 3 075 303 A1 10/2016
(Continued)

OTHER PUBLICATIONS

Tabernero J, Ohlendorf A, Fischer MD, Bruckmann AR, Schiefer U, Schaeffel F. Peripheral refraction profiles in subjects with low foveal refractive errors. Optom Vis Sci. Mar. 2011;88(3):E388-94. doi: 10.1097/OPX.0b013e31820bb0f5. PMID: 21258260 (Year: 2011).*
(Continued)

*Primary Examiner* — Zachary W Wilkes
(74) *Attorney, Agent, or Firm* — Xsensus LLP

(57) ABSTRACT

An ophthalmologic information processing apparatus includes an acquisition unit, a tissue specifying unit, and a specifying unit. The acquisition unit is configured to acquire a tomographic image of a subject's eye formed based on scan data acquired using an optical system for performing optical coherence tomography on the subject's eye. The tissue specifying unit is configured to acquire first shape data representing shape of a tissue of the subject's eye by performing segmentation processing on the tomographic image. The specifying unit is configured to specify a low sensitivity component having a small variation with respect to a change in a position of the optical system with respect to the subject's eye from the first shape data, and to obtain second shape data representing shape of the tissue based on the specified low sensitivity component.

22 Claims, 9 Drawing Sheets

(51) Int. Cl.
*A61B 3/12* (2006.01)
*A61B 3/103* (2006.01)
*A61B 5/00* (2006.01)

(52) U.S. Cl.
CPC .......... *A61B 3/103* (2013.01); *A61B 3/12* (2013.01); *A61B 5/0066* (2013.01); *G06T 2207/10101* (2013.01); *G06T 2207/30041* (2013.01)

(56) References Cited

U.S. PATENT DOCUMENTS

| | | | | |
|---|---|---|---|---|
| 8,517,537 | B2* | 8/2013 | Suehira | A61B 3/102 351/208 |
| 8,684,528 | B2* | 4/2014 | Fujimura | G06T 7/0012 351/206 |
| 8,712,505 | B2* | 4/2014 | Ishikawa | A61B 3/102 600/476 |
| 9,025,844 | B2* | 5/2015 | Iwase | G06T 7/33 382/131 |
| 9,149,181 | B2* | 10/2015 | Matsumoto | A61B 3/102 |
| 9,706,914 | B2 | 7/2017 | Bagherinia et al. | |
| 10,537,243 | B2* | 1/2020 | Ikegami | A61B 3/0025 |
| 2008/0100612 | A1 | 5/2008 | Dastmalchi et al. | |
| 2010/0189334 | A1* | 7/2010 | Tomidokoro | A61B 3/1225 382/131 |
| 2012/0002164 | A1 | 1/2012 | Yamamoto et al. | |
| 2012/0069298 | A1 | 3/2012 | Ng | |
| 2013/0010259 | A1 | 1/2013 | Carnevale | |
| 2013/0242259 | A1 | 9/2013 | Hacker et al. | |
| 2015/0085252 | A1 | 3/2015 | Fujimura et al. | |
| 2015/0366450 | A1 | 12/2015 | Ren et al. | |
| 2016/0331224 | A1 | 11/2016 | Uji et al. | |
| 2016/0345822 | A1 | 12/2016 | Fujimura et al. | |
| 2017/0127936 | A1 | 5/2017 | Iwase et al. | |
| 2017/0135568 | A1 | 5/2017 | Charles | |
| 2017/0181620 | A1 | 6/2017 | Andrews et al. | |
| 2017/0245756 | A1 | 8/2017 | Hayashi et al. | |
| 2018/0192870 | A1 | 7/2018 | Inao et al. | |
| 2018/0289257 | A1 | 10/2018 | Ikegami | |

FOREIGN PATENT DOCUMENTS

| | | |
|---|---|---|
| JP | 2013-248376 A | 12/2013 |
| JP | 2016-77774 A | 5/2016 |
| JP | 2018-175258 A | 11/2018 |

OTHER PUBLICATIONS

Sarah Tick, Florence Rossant, Itebeddine Ghorbel, Alain Gaudric, José-Alain Sahel, Philippe Chaumet-Riffaud, Michel Paques; Foveal Shape and Structure in a Normal Population. Invest. Ophthalmol. Vis. Sci. 2011;52(8):5105-5110. doi: https://doi.org/10.1167/iovs.10-7005 (Year: 2011).*
Office Action dated Sep. 17, 2020, in corresponding U.S. Appl. No. 16/377,263, 27 pages.
Verkicharla et al., "Eye shape and retinal shape, and their relation to peripheral refraction", The Journal of the college of optometrists, 2012, vol. 32, pp. 184-199.
Smth et al., "Relative peripheral hyperopic defocus alters central refractive development in infant monkeys", Sep. 2009, vol. 49 No. 19, pp. 1-15.
Extended European Search Report dated Jun. 9, 2020, issued in corresponding European Patent Application No. 19219988.3, 7 pages.
Extended European Search Report dated Jun. 9, 2020 in European Patent Application No. 19219987.5, 8 pages.
Extended European Search Report dated Jun. 9, 2020 in European Patent Application No. 19219979.2, 8 pages.
Office Action dated Mar. 25, 2021, in corresponding U.S. Appl. No. 16/377,263, 20 pages.

* cited by examiner

OPHTHALMOLOGIC INFORMATION PROCESSING APPARATUS, OPHTHALMOLOGIC APPARATUS AND OPHTHALMOLOGIC INFORMATION PROCESSING METHOD

CROSS-REFERENCE TO RELATED APPLICATION

This application is based upon and claims the benefit of priority from U.S. Provisional Application No. 62/793,044, filed Jan. 16, 2019 the entire contents of which are incorporated herein by reference.

FIELD

Embodiments according to present invention described herein relate to an ophthalmologic information processing apparatus, an ophthalmologic apparatus, and an ophthalmologic information processing method.

BACKGROUND

In recent years, as one of the causes of myopia progress, a possibility that myopia may progress as the retina tries to extend to the back side due to the focal point of the peripheral visual field being on the back side (sclera side) of the retinal surface has been reported (for example, Earl L. Smith et al. "Relative peripheral hyperoptic defocus alters central refractive development in infant monkeys", Vision Research, September 2009, 49 (19), pp. 2386-2392).

In order to suppress such myopia progress, eyeglasses and contact lenses, which move the focal position of the central visual field to the near side (cornea side) by increasing the refractive power of the peripheral visual field, have been developed. Further, refractive surgeries such as the wavefront-guided LASIK, which is performed based on wavefront aberration measured in advance, are also performed. Therefore, in such high-performance refractive correction, measuring accurately the refractive power of the peripheral visual field is required.

In addition, some types of eyeball shape have been ascertained (for example, Pavan K Verkicharia et al. "Eye shape and retinal shape, and their relation to peripheral refraction", Ophthalmic & Physiological Optics, 32 (2012), pp. 184-199).

Such eyeball shapes also include types of shapes common to people with myopia and the like. It is considered effective to measure the change of the shape with myopia progress and to feed back the measurement result to ways to cope with the myopia progress.

SUMMARY

One aspect of some embodiments is an ophthalmologic information processing apparatus including: an acquisition unit configured to acquire a tomographic image of a subject's eye formed based on scan data acquired using an optical system for performing optical coherence tomography on the subject's eye; a tissue specifying unit configured to acquire first shape data representing shape of a tissue of the subject's eye by performing segmentation processing on the tomographic image; and a specifying unit configured to specify a low sensitivity component having a small variation with respect to a change in a position of the optical system with respect to the subject's eye from the first shape data, and to obtain second shape data representing shape of the tissue based on the specified low sensitivity component.

Another aspect of some embodiments is an ophthalmologic information processing apparatus including: an acquisition unit configured to acquire a tomographic image of a subject's eye formed based on scan data acquired using an optical system for performing optical coherence tomography on the subject's eye; a tissue specifying unit configured to acquire first shape data representing shape of a tissue of the subject's eye by performing segmentation processing on the tomographic image; and a specifying unit configured to specify a high sensitivity component having a large variation with respect to a change in a position of the optical system with respect to the subject's eye from the first shape data, and to obtain second shape data representing shape of the tissue by removing the specified high sensitivity component from the first shape data.

Further another aspect of some embodiments is an ophthalmologic apparatus including: the optical system; a movement mechanism that moves the subject's eye and the optical system relative to each other; and the ophthalmologic information processing apparatus described in any one of the above.

Further another aspect of some embodiments is an ophthalmologic information processing method including: an acquisition step that acquires a tomographic image of a subject's eye formed based on scan data acquired using an optical system for performing optical coherence tomography on the subject's eye; a tissue specifying step that acquires first shape data representing shape of a tissue of the subject's eye by performing segmentation processing on the tomographic image; and a specifying step that specifies a low sensitivity component having a small variation with respect to a change in a position of the optical system with respect to the subject's eye from the first shape data, and obtains second shape data representing shape of the tissue based on the specified low sensitivity component.

Further another aspect of some embodiments is an ophthalmologic information processing method including: an acquisition step that acquires a tomographic image of a subject's eye formed based on scan data acquired using an optical system for performing optical coherence tomography on the subject's eye; a tissue specifying step that acquires first shape data representing shape of a tissue of the subject's eye by performing segmentation processing on the tomographic image; and a specifying step that specifies a high sensitivity component having a large variation with respect to a change in a position of the optical system with respect to the subject's eye from the first shape data, and obtains second shape data representing shape of the tissue by removing the specified high sensitivity component from the first shape data.

DETAILED DESCRIPTION

Figure 1:
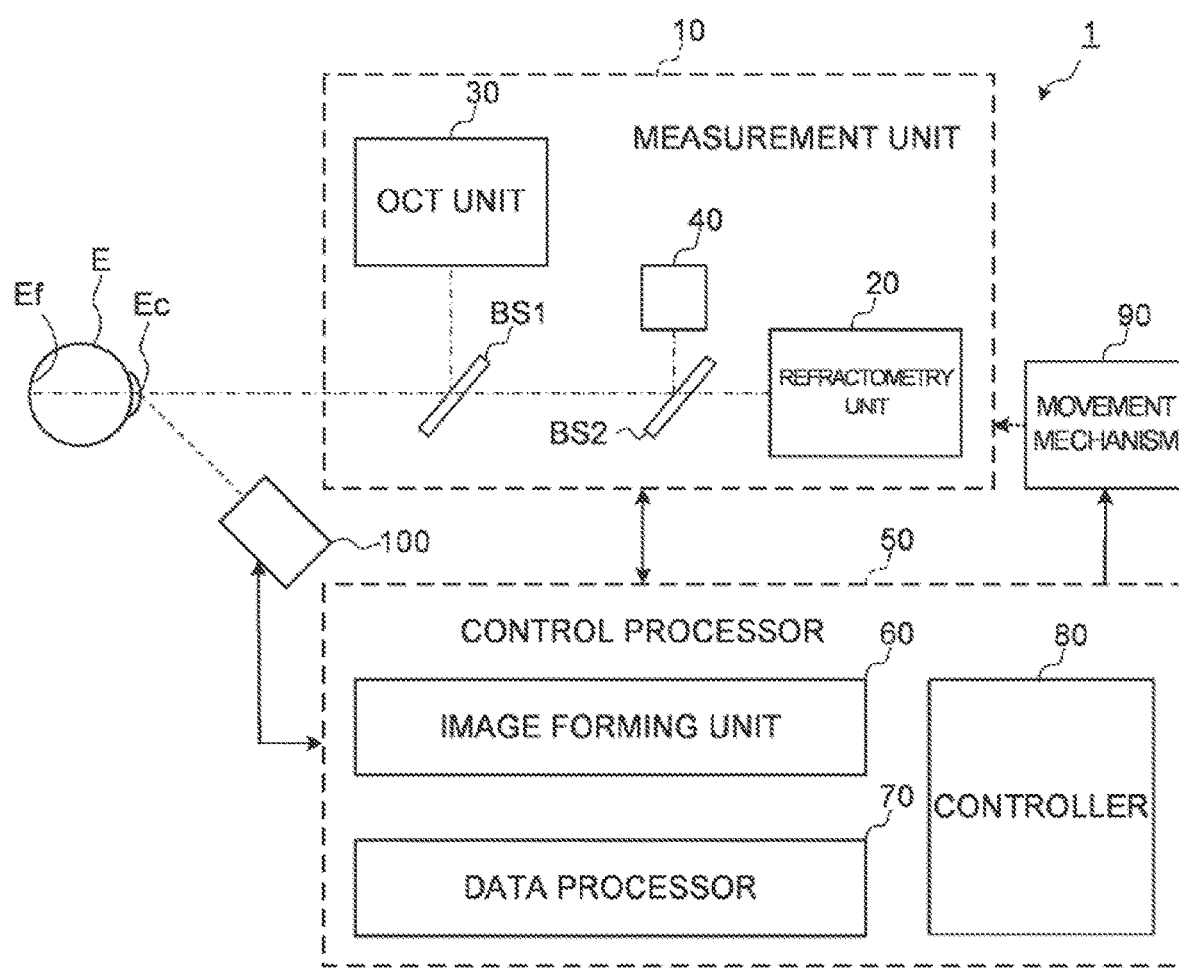
FIG. 1 is a schematic diagram illustrating an example of the configuration of an ophthalmologic apparatus according to the embodiments.

In general ophthalmologic apparatuses, a fixation target is projected onto a measurement optical axis. Thereby, the refractive power near the fovea of the retina is measured. In this case, taking into account the shape of the tissue in the fundus or the like (shape of the eyeball), it is possible to obtain the refractive power of the peripheral visual field from the refractive power of the vicinity of the fovea.

However, when a tomographic image of a subject's eye is acquired using optical coherence tomography for the purpose of measuring the shape of the tissue in the fundus or the like, it is difficult to acquire the tomographic image with high reproducibility due to the amount of misalignment of alignment by the motion of the eye.

According to some embodiments of the present invention, a new technique for specifying shape of a tissue of a subject's eye with high reproducibility and high accuracy can be provided.

Referring now to the drawings, exemplary embodiments of an ophthalmologic information processing apparatus, an ophthalmologic apparatus, an ophthalmologic information processing method, and a program according to the present invention are described below. Any of the contents of the documents cited in the present specification and arbitrary known techniques may be applied to the embodiments below.

An ophthalmologic information processing apparatus according to embodiments acquires a tomographic image of a subject's eye. For example, the tomographic image is acquired by performing optical coherence tomography on the subject's eye using an external ophthalmologic apparatus. The ophthalmologic information processing apparatus analyzes the acquired tomographic image to obtain shape data (first shape data) of a predetermined tissue, and obtains true shape data (second shape data) of the tissue from the obtained shape data. The true shape of the tissue can be specified (extrapolated, predicted) from the obtained shape data.

The shape data obtained by analyzing the tomographic image includes a high sensitivity component and a low sensitivity component, the high sensitivity component having a large variation with respect to a change (infinitesimal changes) in a position of an optical system for performing OCT on the subject's eye, the low sensitivity component having a small variation with respect to the change in the position of the optical system. In some embodiments, the ophthalmologic information processing apparatus specifies the low sensitivity component from the shape data obtained by analyzing the tomographic image, and specifies the true shape data of the tissue based on the specified low sensitivity component. In some embodiments, the ophthalmologic information processing apparatus specifies the high sensitivity component from the shape data obtained by analyzing the tomographic image, and specifies the true shape data of the tissue by removing the high sensitivity component from the shape data.

In some embodiments, the shape of a predetermined layer region is specified by one-dimensional, two-dimensional, or three-dimensional shape data of the predetermined layer region obtained by analyzing the tomographic image. The ophthalmologic apparatus according to some embodiments includes the above ophthalmologic information processing apparatus, and realizes the function of the ophthalmologic information processing apparatus.

By specifying the shape of the predetermined tissue of the subject's eye from the tomographic image or the shape data, the influence of an amount of misalignment of alignment (amount of alignment error) of the subject's eye with respect to the optical system for performing OCT can be reduced, and the shape of the tissue of the subject's eye can be specified with high reproducibility and high accuracy.

Examples of the shape of the tissue in the subject's eye include a shape of a tissue in the anterior segment, a shape of a tissue in the posterior segment, and the like. Examples of the shape of the tissue in the anterior segment include a shape of a cornea, a shape of an iris, a shape of a crystalline lens, a shape of a ciliary body, a shape of a ciliary zonule, a shape of an angle, and the like. Examples of the shape of the tissue in the posterior segment include a shape of the fundus (a predetermined layer region in the fundus), and the like. Hereinafter, shape of a predetermined layer region in a fundus will be described as an example of the shape of the tissue according to the embodiments. In some embodiments, the shape of the layer region in the fundus can be specified as the shape of the fundus. Examples of the layer region of the fundus include the inner limiting membrane, the nerve fiber layer, the ganglion cell layer, the inner plexiform layer, the inner nuclear layer, the outer plexiform layer, the outer nuclear layer, the external limiting membrane, the photoreceptor layer, the retinal pigment epithelium layer, the choroid, the sclera, the boundary surfaces of each layer region, and the like. However, the embodiments described after can be applied to the shape of any site of the eyeball other than the fundus. Further, in the following embodiments, shape data representing the shape of the fundus may be referred to as a shape profile. The shape profile is data representing a change in shape in a predetermined one-dimensional direction, a predetermined two-dimensional direction, or a predetermined three-dimensional direction.

The ophthalmologic information processing apparatus according to some embodiments calculates (extrapolates) a refractive power of a peripheral region outside a region including a fovea in the fundus using the shape of the fundus specified as described above. For example, the ophthalmologic information processing apparatus calculates the refractive power of the peripheral region outside the region including the fovea, based on a refractive power of the region including the fovea of the subject's eye and the specified shape of the fundus.

The ophthalmologic information processing apparatus according to the embodiments can calculate the refractive power of the above region using parameters of an eyeball model such as a known schematic eye (parameters representing optical characteristics of the eyeball). Examples of the parameter include axial length data, anterior chamber depth data, crystalline lens data (curvature of crystalline lens, thickness of crystalline lens, or the like) representing a shape of a crystalline lens, corneal shape data (corneal curvature radius, corneal thickness, or the like), and the like. The ophthalmologic information processing apparatus can build (form) a new eyeball model by replacing a part of the parameters of the eyeball model with the measured value of the subject's eye, and calculate the refractive power of the above region using the built new eyeball model. In some embodiments, the above parameter is obtained from an electronic health record system, a medical image archiving system, an external apparatus, or the like.

An ophthalmologic information processing method according to the embodiments includes one or more steps for realizing the processing executed by a processor (computer) in the ophthalmologic information processing apparatus according to the embodiments. A program according to the embodiments causes the processor to execute each step of the ophthalmologic information processing method according to the embodiments.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes the function according to the embodiments, for example, by reading out a computer program stored in a storage circuit or a storage device and executing the computer program.

In this specification, images acquired using OCT may be collectively referred to as "OCT images". Further, a measuring action for forming an OCT image is sometimes referred to as an OCT measurement. Data acquired by performing OCT scan is sometimes referred to as scan data.

Hereinafter, the case where the ophthalmologic apparatus according to the embodiments includes the ophthalmologic information processing apparatus will be described. The ophthalmologic apparatus is configured to acquire a tomographic image of the subject's eye by performing OCT on the subject's eye E. However, the ophthalmologic information processing apparatus according to the embodiments may be configured to acquire scan data (OCT data), the tomographic image, the shape profile described after, or the like from an external ophthalmologic apparatus.

The ophthalmologic apparatus according to some embodiments includes an OCT apparatus and is configured to perform registration between the subject's eye and an optical system for performing OCT. The ophthalmologic apparatus according to some embodiments further includes an objective refractometry apparatus. The ophthalmologic apparatus according to some embodiments includes a device (communication interface, input/output interface, etc.) that receives data from an external apparatus or a recording medium.

That is, the ophthalmologic apparatus according to the embodiments may be, for example, any one of the following: (A) an inspection apparatus that includes an objective refractometry apparatus (refractometry unit) and an OCT apparatus (OCT unit): (B) an inspection apparatus that does not include an objective refractometry apparatus (refractometry unit) but includes an OCT apparatus (OCT unit): (C) an information processing apparatus that includes neither an objective refractometry apparatus (refractometry unit) nor an OCT apparatus (OCT) unit.

Hereinafter, the left/right direction (i.e., horizontal direction) which is orthogonal to the optical axis (measurement optical axis, inspection optical axis) of the optical system of the ophthalmologic apparatus is regarded as the x direction, the up/down direction (i.e., vertical direction) which is orthogonal to the axis is regarded as the y direction, and the optical axis direction (i.e., depth direction, front-back direction) is regarded as the z direction.

<Configuration>

Figure 2:
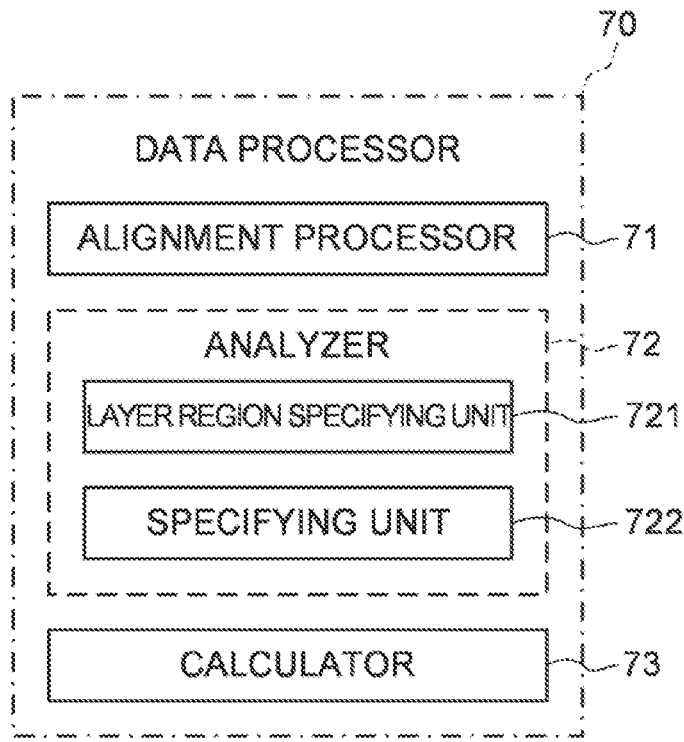
FIG. 2 is a schematic diagram illustrating an example of the configuration of the ophthalmologic apparatus according to the embodiments.
Figure 3:
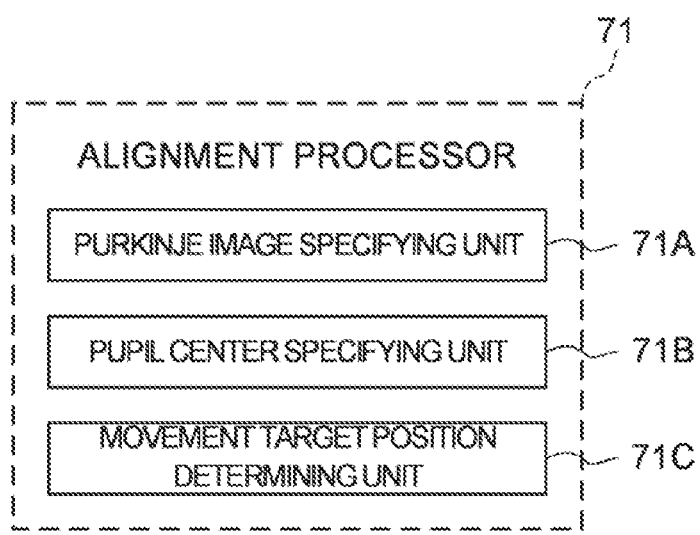
FIG. 3 is a schematic diagram illustrating an example of the configuration of the ophthalmologic apparatus according to the embodiments.
Figure 4:
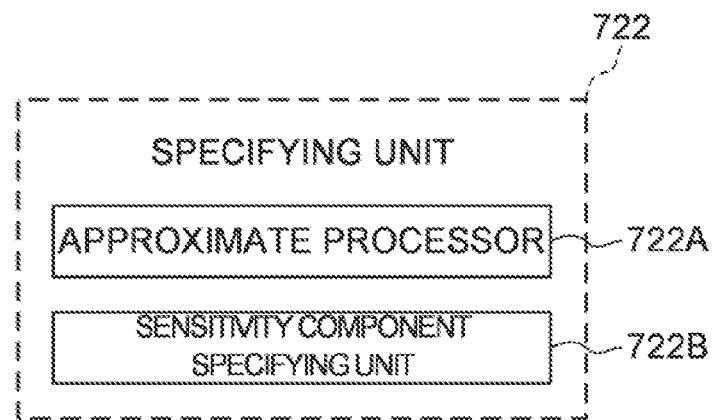
FIG. 4 is a schematic diagram illustrating an example of the configuration of the ophthalmologic apparatus according to the embodiments.
Figure 5:
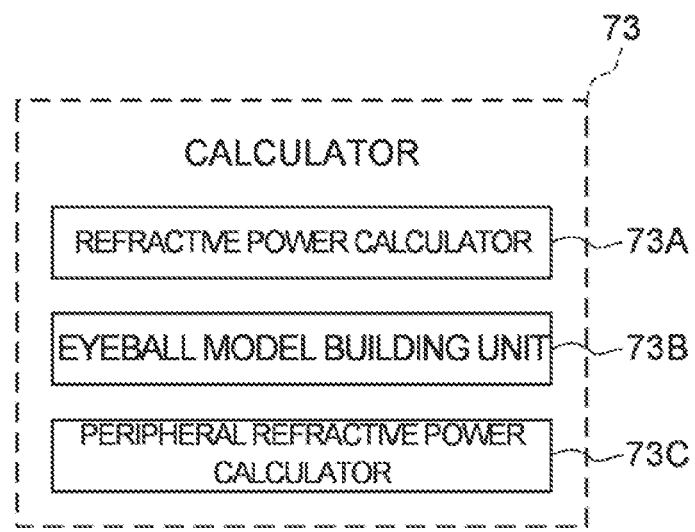
FIG. 5 is a schematic diagram illustrating an example of the configuration of the ophthalmologic apparatus according to the embodiments.

FIGS. 1 to 5 illustrate examples of the configuration of the ophthalmologic apparatus according to the embodiments. FIG. 1 is a schematic block diagram illustrating an example of the configuration of the ophthalmologic apparatus according to the embodiments. FIG. 2 shows a functional block diagram representing a configuration example of a data processor 70 in FIG. 1. FIG. 3 shows a functional block diagram representing a configuration example of an alignment processor 71 in FIG. 2. FIG. 4 shows a functional block diagram representing a configuration example of a specifying unit 722 in FIG. 2. FIG. 5 shows a functional block diagram representing a configuration example of a calculator 73 in FIG. 2.

The ophthalmologic apparatus 1 is an inspection apparatus that includes an objective refractometry apparatus (refractometry unit) and an OCT apparatus (OCT unit). The ophthalmologic apparatus 1 includes a measurement unit 10, a control processor 50, a movement mechanism 90, and an imaging unit 100. The measurement unit 10 includes a refractometry unit 20, an OCT unit 30, an alignment light projection unit 40, and beam splitters BS1 and B2. The control processor 50 includes an image forming unit 60, a data processor 70, and a controller 80.

(Refractometry Unit 20)

The refractometry unit 20 objectively measures a refractive power of a subject's eye E under the control of the controller 80. The refractometry unit 20 includes an optical system provided with one or more optical members for performing objective refractometry. The refractometry unit 20 has the same configuration as a known refractometer, for example. An exemplary refractometer (not shown in the figure) includes a projection system and a light reception system as disclosed in Japanese Unexamined Patent Application Publication No. 2016077774.

A projection system of the refractometry unit 20 is configured to project light emitted from a light source onto a fundus Ef of the subject's eye E. The projection system projects the light from the light source onto the fundus Ef through a collimate lens, a focusing lens, a relay lens, a pupil lens, a perforated prism, a decentered prism (eccentric prism an objective lens, and the like, for example.

A light reception system of the refractometry unit 20 projects reflected light from the fundus Ef onto an imaging element through the objective lens, the decentered prism, the perforated prism, other pupil lenses, other relay lenses, another focusing lens, a conical prism, an imaging lens, and the like. Thereby, a ring pattern image formed on an imaging surface of the imaging element is detected.

In some embodiments, the refractometry unit 20 is configured to project ring-shaped light onto the fundus Ef and to detect the ring pattern image formed by the reflected light from the fundus Ef. In some embodiments, the refractometry unit 20 is configured to project bright spot onto the fundus Ef, to convert the reflected light from the fundus Ef into ring-shaped light, and to detect the ring pattern image formed by the converted ring-shaped light.

(OCT Unit 30)

The OCT unit 30 acquires OCT data (scan data) by applying OCT scan to the subject's eye E under the control of the controller 80. The OCT data may be interference signal data, reflection intensity profile data obtained by applying Fourier transformation to the interference signal data, image data obtained by imaging the reflection intensity profile data.

The OCT method that can be performed by the OCT unit 30 is typically Fourier domain OCT. Fourier domain OCT may be either spectral domain OCT or swept source OCT. The swept source OCT is a method that splits light from a wavelength tunable light source into measurement light and reference light; superposes returning light of the measurement light projected onto the subject's eye from the subject's eye with the reference light to generate interference light; detects the interference light with an optical detector; and applies the Fourier transformation etc. to detection data (interference signal data) acquired in accordance with the sweeping of wavelengths and the scanning of the measurement light to form reflection intensity profile data. On the other hand, the spectral domain OCT is a method that splits light from a low coherence light source (broadband light source) into measurement light and reference light; superposes returning light of the measurement light projected onto the subject's eye from the subject's eye with the reference light to generate interference light; detects the spectral distribution of the interference light with a spectrometer; and applies the Fourier transformation etc. to detection data (interference signal data) detected by the spectrometer to form reflection intensity profile data That is, the swept source OCT is an OCT method for acquiring the spectral distribution by time division, and the spectral domain OCT is an OCT method for acquiring the spectral distribution by space division.

The OCT unit 30 includes an optical system provided with one or more optical members for performing OCT measurement. The OCT unit 30 has the same configuration as a known OCT apparatus, for example. An exemplary OCT apparatus (not shown in the figure) includes a light source, an interference optical system, a scan system, and a detection system as disclosed in Japanese Unexamined Patent Application Publication No. 2016-077774.

Light output from the light source is split into the measurement light and the reference light by the interference optical system. The reference light is guided by a reference arm. The measurement light is projected onto the subject's eye E (for example, the fundus Ef) through a measurement arm. The measurement arm is provided with the scan system. The scan system includes, for example, an optical scanner and is capable of deflecting the measurement light one-dimensionally or two-dimensionally. The optical scanner includes one or more galvano scanners. The scan system deflects the measurement light according to a predetermined scan mode.

The controller 80 described after can control the scan system according to the scan mode. Examples of the scan mode include line scan, raster scan (three-dimensional scan), circle scan, concentric scan, radial scan, cross scan, multi cross scan, spiral scan, and the like. The line scan is a scan pattern along a linear trajectory. The raster scan is a scan pattern consisting of a plurality of line scans arranged parallel to one another. The circle scan is a scan pattern along a circular trajectory. The concentric scan is a scan pattern consisting of a plurality of circle scans arranged concentrically. The radial scan is a scan pattern consisting of a plurality of line scans arranged radially. The cross scan is a scan pattern consisting of two line scans arranged orthogonal to one another. The multi cross scan is a scan pattern consisting of two line scan groups (for example, each groups includes five lines parallel to one another) orthogonal to one another. The spiral scan is a scan pattern extending in a spiral manner from the center.

The measurement light projected onto the fundus Ef is scattered and reflected at various depth positions (layer boundaries, etc.) of the fundus Ef. The returning light of the measurement light from the subject's eye E is combined with the reference light by the interference optical system. The returning light of the measurement light and the reference light generates the interference light according to the principle of superposition. This interference light is detected by the detection system. The detection system typically includes the spectrometer in case of spectral domain OCT. The detection system typically includes a balanced photodiode and a data acquisition system (DAQ) in case of swept source OCT.

(Alignment Light Projection Unit 40)

The alignment light projection unit 40 projects alignment light for performing position matching between the subject's eye E and the measurement unit 10 (OCT unit, the optical system of the apparatus). The alignment light projection unit 40 includes an alignment light source and a collimator lens. An optical path of the alignment light projection unit 40 is coupled with an optical path of the refractometry unit 20 by the beam splitter BS2. Light emitted from the alignment light source passes through the collimator lens, is reflected by the beam splitter BS2, and is projected onto the subject's eye E through the optical path of the refractometry unit 20.

In some embodiments, as disclosed in Japanese Unexamined Patent Application Publication No. 2016-077774, the reflected light from the cornea Ec (anterior segment) of the subject's eye E is guided to the light reception system of the refractometry unit 20 through the optical path of the refractometry unit 20.

An image (bright spot image) based on the reflected light by the cornea Ec of the subject's eye E is included in the anterior segment image acquired by the imaging unit 100. For example, the control processor 50 controls the display unit (not shown in Figure) to display an alignment mark and the anterior segment image including the bright spot image on the display screen of the display unit. In the case of performing XY alignment (alignment in vertical and horizontal directions) manually, a user can perform an operation for moving the optical system so as to guide the bright spot image in the alignment mark. In the case of performing Z alignment (alignment in front-back direction) manually, a user can perform the operation for movement of the optical system while referring to the anterior segment image displayed on the display screen of the display unit. In the case of performing alignment automatically, the controller 80 controls the movement mechanism 90 to relatively move the measurement unit 10 (optical system) with respect to the subject's eye E so as to cancel the displacement between the alignment mark and the position of the bright spot image. Further, the controller 80 can control the movement mechanism 90 to move the measurement unit 10 (optical system)

with respect to the subject's eye E so as to satisfy a predetermined alignment completion condition based on a position of a predetermined site (for example, pupil center position) of the subject's eye E and the position of the bright spot image.

(Beam Splitter BS1)

The beam splitter BS1 coaxially couples the optical path of the optical system (interference optical system, etc.) of the OCT unit 30 with the optical path of the optical system (projection system and light reception system) of the refractometry unit 20. For example, a dichroic mirror is used as the beam splitter BS1.

(Beam Splitter BS2)

The beam splitter BS2 coaxially couples the optical path of the optical system of the alignment light projection unit 40 with the optical path of the optical system (projection system and light reception system) of the refractometry unit 20. For example, a half mirror is used as the beam splitter BS2.

In some embodiments, the ophthalmologic apparatus 1 has a function (fixation projection system) that presents a fixation target, which is used for guiding a visual line of the subject's eye, to the subject's eye E under the control of the controller 80. The fixation target may be an internal fixation target presented to the subject's eye E or an external fixation target presented to the fellow eye. In some embodiments, an optical path of the fixation projection system and the optical path of the interference optical system of the OCT unit 30 are configured to coaxially coupled by an optical path coupling member (for example, beam splitter) arranged between the OCT unit 30 and the beam splitter BST A projection position of the fixation target in the fundus Ef projected by the fixation target projection system can be changed under the control of the controller 80. In some embodiments, the fixation target is projected onto the measurement optical axes of coaxially coupled the optical system of the refractometry unit 20 and the optical system of the OCT unit 30. In some embodiments, the fixation target is projected at a position deviated from the measurement optical axis on the fundus Ef.

(Imaging Unit 100)

The imaging unit 100 includes one or more anterior segment cameras for imaging the anterior segment of the subject's eye E. The imaging unit 100 acquires the anterior segment image(s) which is (are) the front image of the subject's eye E. In some embodiments, at least one anterior segment illumination light source (infrared light source or the like) is provided in the vicinity of the one or more anterior segment cameras. For example, for each anterior segment cameras, the anterior segment illumination light source is provided in the upper vicinity and the lower vicinity of the anterior segment camera, respectively.

The ophthalmologic apparatus 1 can perform position matching (alignment) of the measurement unit 10 (optical system) with respect to the subject's eye E using the front image acquired by the imaging unit 100. In some embodiments, the ophthalmologic apparatus 1 specifies a three-dimensional position of the subject's eye E by analyzing the front image acquired by imaging the anterior segment of the subject's eye E, and performs position matching by relatively moving the measurement unit 10 based on the specified three-dimensional position. In some embodiments, the ophthalmologic apparatus 1 performs position matching so as to cancel the displacement between a characteristic position of the subject's eye E and a position of the image formed by the alignment light projected by the alignment light projection unit 40.

As described above, the imaging unit 100 includes one or more anterior segment cameras. In case that the imaging unit 100 includes a single anterior segment camera, the ophthalmologic apparatus 1 analyzes the acquired front image, and specifies a two-dimensional position of the subject's eye E in a plane orthogonal to the optical axis of the measurement unit 10 (plane defined by the horizontal direction (X direction) and the vertical direction (Y direction)), in this case, the alignment optical system for specifying a position of the subject's eye E in the optical axis direction of the measurement unit 10 is provided in the ophthalmologic apparatus 1. Examples of such an alignment optical system includes an optical system of an optical lever system as disclosed in Japanese Unexamined Patent Application Publication No. 2016-077774. The ophthalmologic apparatus 1 can specify the three-dimensional position of the subject's eye E from the position of the subject's eye in the (measurement) optical axis of the measurement unit 10 and the above two-dimensional position, using alignment optical system like this.

In case that the imaging unit 100 includes two or more anterior segment cameras, two or more anterior segment cameras photograph the anterior segment of the subject's eye E from different directions. The two or more anterior segment cameras can substantially simultaneously photograph the anterior segment from two or more different directions. The phrase "substantially simultaneously" indicates that the deviation in photography timings at a level where the eye movement is negligible is allowed in the photography with two or more anterior segment cameras. Thereby, images of the subject's eye E located in substantially the same position (orientation) can be acquired by the two or more anterior segment cameras. The ophthalmologic apparatus 1 analyzes the front images of the subject's eye E, specifies the characteristic position of the subject's eye E, and specifies the three-dimensional position of the subject's eye E from the positions of the two or more anterior segment cameras and the characteristic position.

Photography using the two or more anterior segment cameras may be moving image photography or still image photography. In the case of moving image photography, substantially simultaneous photography of the anterior segment as described above can be realized by performing control for synchronizing photography start timings, controlling the frame rates or the capture timings of respective frames, or the like. On the other hand, in the case of still image photography, this can be realized by performing control for synchronizing photography timings.

In the following, it is assumed that the imaging unit 100 includes two anterior segment cameras. Each of the two anterior segment cameras is located at a position off the measurement optical axis (optical axis of the OCT unit 30) as disclosed in Japanese Unexamined Patent Application Publication No. 2013-248376. In some embodiments, one of the two anterior segment cameras is an imaging element in the light reception system of the refractometry unit 20.

(Control Processor 50)

The control processor 50 performs various calculations and various controls for operating the ophthalmologic apparatus 1. The control processor 50 includes one or more processors and one or more storage devices. Examples of the storage device include random access memory (RAM), read only memory (ROM), hard disk drive (HDD), solid state drive (SSD), and the like. The storage device stores various computer programs. The calculation and control according to the present examples are realized by operating the processor based on it.

(Image Forming Unit 60)

The image forming unit 60 forms an image (tomographic image, etc.) of the subject's eye E based on the scan data acquired by performing OCT on the subject's eye E. The image forming unit 60 builds OCT data (typically, image data) based on detection data detected by the detection system of the OCT unit 30. The image forming unit 60, similar to conventional OCT data processing, builds the reflection intensity profile data in A line (path of the measurement light in the subject's eye E), by applying filter processing, fast Fourier transformation (FFT), and the like to the detection data. In addition, the image forming unit 60 builds the image data of each A line (A scan data) by applying image processing (image expression) to this reflection intensity profile data. In some embodiments, the function of the image forming unit 60 is realized by a processor.

In some embodiments, at least part of the function of the image forming unit 60 is provided in the OCT unit 30.

(Data Processor 70)

The data processor 70 executes various data processing. The data processor 70 can build (form) B scan data by arranging a plurality of A scan data according to the scan mode performed by the scan system. In some embodiments, the data processor 70 performs superposition processing of the two or more B scan data. The data processor 70 can build stack data by arranging a plurality of B scan data according to the scan mode performed by the scan system. The data processor 70 build volume data (voxel data) from the stack data. The data processor 70 can render the stack data or the volume data Examples of rendering method include volume rendering, multi-planar reconstruction (MPR), surface rendering, projection, and the like.

The data processor 70 can execute processing for performing position matching of the measurement unit 10 with respect to the subject's eye E. Examples of the processing for performing position matching (registration) include analysis processing of the front image of the subject's eye E acquired using the imaging unit 100, calculation processing of the position of the subject's eye E, calculation processing of the displacement of the measurement unit 10 with respect to the subject's eye E, and the like.

In addition, the data processor 70 can acquire shape data (shape profile) representing the shape of the fundus Ef of the subject's eye E from the tomographic image of the subject's eye E obtained by performing OCT measurement after position matching (alignment), and generate shape data representing the true shape of the fundus Ef from the acquired shape data. For example, the shape data representing the true shape of the fundus Ef is obtained by specifying the low sensitivity component for an alignment error from the acquired shape data. Further, the data processor 70 can calculate refractive power of a peripheral region of a region including a fovea of the subject's eye E using the specified shape of the fundus Ef (shape data representing the true shape of the fundus ED.

As shown in FIG. 2, such as the data processor 70 includes an alignment processor 71, an analyzer 72, and a calculator 73.

(Alignment Processor 71)

The alignment processor 71 executes processing for performing position matching (alignment) of the measurement unit 10 with respect to the subject's eye E. In some embodiments, the alignment processor 71 corrects distortion of the photographic images captured by the anterior segment cameras, and executes processing for performing above position matching using the captured photographic image(s) whose distortion has (have) been corrected. In this case, the alignment processor 71 corrects the distortion of the photographic image(s) based on the aberration information stored in a storage unit provided in the control processor 50 or the data processor 70. This processing is performed by, for example, known image processing technology based on a correction factor for correcting distortion aberration.

As shown in FIG. 3, the alignment processor 71 includes a Purkinje image specifying unit 71A, a pupil center specifying unit 71B, and a movement target position determining unit 71C.

(Purkinje Image Specifying Unit 71A)

By projecting the alignment light onto the anterior segment of the subject's eye E using the alignment light projection unit 40, a Purkinje image is formed. The Purkinje image is formed in a position displaced from the corneal apex in the optical axis direction (z direction) by half of the radius of the corneal curvature.

The anterior segment onto which the alignment light is projected is substantially simultaneously photographed by the two anterior segment cameras. The Purkinje image specifying unit 71A specifies the Purkinje image (image region corresponding to the Purkinje image) by analyzing each of the two photographic images substantially simultaneously acquired using the two anterior segment cameras. This specifying processing includes, for example as in the conventional case, a threshold processing related to a pixel value for searching for a bright spot (pixel having high brightness) corresponding to the Purkinje image. Thereby, the age regions in the photographic images corresponding to the Purkinje image are specified.

The Purkinje image specifying unit 71A can obtain a position of a representative point in the image region corresponding to the Purkinje image. The representative point may be a center point or a center of gravity point of the image region, for example. In this case, the Purkinje image specifying unit 71A can obtain an approximate circle or an approximate ellipse of the periphery of the image region, and can obtain the center point or the center of gravity point of the approximate circle or the approximate ellipse.

Each of the two photographic images is an image obtained by photographing the anterior segment from a diagonal direction. In each of the photographic images, a pupil region and a Purkinje image are depicted. The Purkinje image specifying Unit 71A specifies the Purkinje images in the two photographic images.

Here, the two photographic images are images obtained by photographing from directions different front the optical axis of the measurement unit 10 (objective lens). When XY alignment is substantially matched, the Purkinje images in the two photographic images are formed on the optical axis of the measurement unit 10.

Visual angles angles with respect to the optical axis of the measurement unit 10) of the two anterior segment cameras are known and the photographing magnification is also known. Thereby, the relative position (three-dimensional position in actual space) of the Purkinje image formed in the anterior segment with respect to the ophthalmologic apparatus 1 (imaging unit 100) can be obtained based on the positions of the Purkinje images in the two photographic images.

Further, the relative position between the characteristic position f the subject's eye E and the Purkinje image formed in the anterior segment can be obtained based on the relative position (misalignment amount) between the characteristic position of the subject's eye E and the position of the Purkinje image in each of the two photographic images.

The Purkinje image specifying unit 71A specifies the position of the Purkinje image specified as above. The position of the Purkinje image may include at least a position in the x direction (x coordinate value) and a position in the y direction (y coordinate value), or may further include a position in the z direction (z coordinate value).

(Pupil Center Specifying Unit 71B)

The pupil center specifying unit 71B specifies a position in the photographic image corresponding to a predetermined characteristic position of the anterior segment by analyzing each of photographic images (or the images corrected for distortion aberration) obtained by the anterior segment cameras. In the present embodiment, the pupil center of the subject's eye E is specified. It should be noted that the center of gravity of the pupil may be obtained as the pupil center. It is also possible to configure such that the characteristic position other than the pupil center (the center of gravity of the pupil) is specified.

The pupil center specifying unit 71B specifies the image region (pupil region) corresponding to the pupil of the subject's eye E based on the distribution of pixel values (luminance values etc.) in the photographic image. Generally, the pupil is represented with lower luminance compared to other sites, and therefore, the pupil region may be specified by searching an image region with low luminance. At this time, the pupil region may be specified by taking the shape of the pupil into consideration. That is, it is possible to configure such that the pupil region is specified by searching for a substantially circular image region with low luminance.

Next, the pupil center specifying unit 71B specifies the center position of the specified pupil region. As mentioned above, the pupil is substantially circular. Accordingly, by specifying the contour of the pupil region and then specifying the center position of an approximate ellipse of this contour, this may be used as the pupil center. Instead, by obtaining the center of gravity of the pupil region, this center of gravity may be used as the pupil center.

Note that, even when other characteristic positions are employed, the position of the characteristic position can be specified based on the distribution of pixel values in the photographic image in the same manner as mentioned above.

The pupil center specifying unit 71B specifies the three-dimensional position of the pupil center of the subject's E, based on the positions of the two anterior segment cameras (and the photographing magnification) and the positions of the specified pupil center in the two photographic images.

For example, the resolution of photographic images obtained by the two anterior segment cameras is expressed by the following expressions.

$xy$ resolution(planar resolution): $\Delta xy = H \times \Delta p / f$ $z$ resolution(depth resolution): $\Delta z = H \times H \times \Delta p / (B \times f)$ Here, the distance (base line length) between the two anterior segment cameras is represented as "B", the distance (photographing distance) between the base line of the two anterior eye cameras and the pupil center of the subject's eye E is represented as "H", the distance (screen distance) between each anterior segment camera and its screen plane is represented as "f", and the pixel resolution is represented as "$\Delta p$".

The pupil center specifying unit 71B applies known trigonometry to the positions of the two anterior segment cameras (these are known) and positions corresponding to the pupil center in the two photographic images, thereby calculating the three-dimensional position of the pupil center.

(Movement Target Position Determining Unit 71C)

The movement target position determining unit 71C determines the movement target position of the measurement unit 10 (optical system of the apparatus) based on the position of the Purkinje image specified by the Purkinje image specifying unit 71A and the position of the pupil center specified by the pupil center specifying unit 71B. For example, the movement target position determining unit 71C obtains the difference between the position of the specified Purkinje image and the position of the specified pupil center, and determines the movement target position so that the obtained difference satisfies a predetermined alignment completion condition.

The controller 80 described after controls the movement mechanism 90 based on the movement target position determined by the movement target position determining unit 71C.

(Analyzer 72)

As shown in FIG. 2, the analyzer 72 includes a layer region specifying unit 721, and a specifying unit 722. The layer region specifying unit 721 specifies a predetermined layer region (a predetermined tissue) in the acquired tomographic image of subject's eye E. The specifying unit 722 specifies the shape of the fundus Ef based on the predetermined layer region specified by the layer region specifying unit 721.

(Layer Region Specifying Unit 721)

The layer region specifying unit 721 specifies the predetermined layer region of the fundus Ef by analyzing the tomographic image of the subject's eye E. Examples of the layer region of the fundus Ef include the inner limiting membrane, the nerve fiber layer, the ganglion cell layer, the inner plexiform layer, the inner nuclear layer, the outer plexiform layer, the outer nuclear layer, the external limiting membrane, the photoreceptor layer, the retinal pigment epithelium layer, the choroid, the sclera, the boundary surfaces of each layer region, and the like.

Processing of specifying the predetermined layer region from the tomographic image typically includes segmentation processing. The segmentation processing is known processing for specifying a partial region in a tomographic image. The layer region specifying unit 721 performs, for example, segmentation processing based on a brightness value of each pixel in the tomographic image. That is, each of the layer regions of the fundus Ef has a characteristic reflectance, and image regions corresponding to these layer regions also have characteristic brightness values. The layer region specifying unit 721 can specify a target image region (layer region) by performing segmentation processing based on these characteristic brightness values.

The layer region specifying unit 721 outputs data representing the shape of the specified predetermined layer region as the shape profile of the layer region. In some embodiments, the shape profile is one-dimensional, two-dimensional, or three-dimensional shape data representing a change in the shape of the fundus Ef in at least one direction of the x direction, the y direction, and the z direction.

For example, the layer region specifying unit 721 can specify the retinal pigment epithelium layer (or OS-RPE boundary surface).

(Specifying Unit 722)

The specifying unit 722 specifies the shape of the fundus Ef from the shape data (shape profile) obtained by the layer region specifying unit 721. Specifically, the specifying unit 722 specifies the shape data representing the true shape from the shape data of the predetermined layer region obtained from the tomographic image acquired by performing OCT measurement. The specifying unit 722 obtains, for example, the shape data representing the true shape based on a component having low sensitivity to an alignment error obtained from the shape data. In some embodiments, the specifying unit 722 generates a new shape profile one-dimensionally (two-dimensionally or three-dimensionally) representing the true shape of the layer region from the shape profile one-dimensionally (two-dimensionally or three-dimensionally) representing the shape of the layer region.

As shown in FIG. 4, such the specifying unit 722 includes an approximate processor 722A and a sensitivity component specifying unit 722B.

(Approximate Processor 722A)

The approximate processor 722A approximates the shape profile representing the shape of the layer region specified by the layer region specifying unit 721 to an expression using the position of the OCT unit 30 with respect to the subject's eye E as a variable, the expression including the high sensitivity component and the low sensitivity component for alignment error (deviation of alignment) of the OCT unit 30 with respect to the subject's eye E. Here, the high sensitivity component means a component with large variation with respect to infinitesimal changes of the alignment error among the shape profile. The low sensitivity component means a component with small variation with respect to infinitesimal changes of the alignment error among the shape profile. The alignment error is represented, for example, by the relative position (relative position in the xy directions) of the measurement optical axis of the OCT unit 30 with respect to the subject's eye E with reference to the alignment reference position when the alignment is completed.

In some embodiments, the low sensitivity component is a component whose variation amount is equal to or less than a first threshold value TH1 (0<TH1) for a predetermined variation amount of the alignment error. In some embodiments, the high sensitivity component is a component whose variation amount is more than a second threshold value TH2 (TH1≤TH2) for a predetermined variation amount of the alignment error.

In some embodiments, the shape profile is approximated to an expression represented using the high sensitivity component and the low sensitivity component. In some embodiments, the shape profile is approximated to an expression represented using the high sensitivity component, the low sensitivity component, and other components.

Further, when the shape profile is expressed, as a variable, with the relative position of the measurement optical axis of the OCT unit 30 with respect to the subject's eye E with reference to the alignment reference position, the asymmetric component of the shape profile is the high sensitivity component. On the other hand, the symmetric component of the shape profile is the low sensitivity component. An odd order component of the above variable is included in the high sensitivity components. Examples of the high sensitivity component include a component representing an inclination, a component representing a distortion, and the like. An even order component of the above variable is included in the low sensitivity components. Examples of the low sensitivity component include a component representing a curvature, and the like.

In the embodiments, the approximate processor 722A is capable of performing polynomial approximation on the shape profile with the component of the relative position of the measurement optical axis of the OCT unit 30 with respect to the subject's eye E as a variable with reference to the alignment reference position. Assuming that the above variable is d, and the coefficients of each order of polynomial are c0, c1, . . . , the polynomial f(d) corresponding to the shape profile is expressed by the following expression.

$$f(d) = c0 \times c1 \times d + c2 \times d^2 + c^3 \times d^3 c4 \times d^4$$

In the above expression, the component representing the inclination corresponds to the first order component of d (i.e., $c1 \times d$). The component representing the curvature corresponds to the second order component of d ($c2 \times d^2$). The component representing the distortion corresponds to the third order component of d (i.e., $c3 \times d^3$).

As described above, the high sensitivity component and the low sensitivity component caused by the variable d can be specified, by polynomial approximation of the shape profile as the variable d performed by the approximate processor 722A.

(Sensitivity Component Specifying Unit 722B)

The sensitivity component specifying unit 722B specifies the low sensitivity component from the expression representing the shape profile obtained by the approximate processing by the approximate processor 722A, and generates the shape profile (shape data) representing true shape of the predetermined layer region based on the specified low sensitivity component.

For example, in the cased that the polynomial f(d) described above is obtained by the approximate processor 722A, the sensitivity component specifying unit 722B specifies the even order component of d (for example, the second order component of d) as the low sensitivity component, and outputs the specified low sensitivity component as the shape profile representing the true shape of the predetermined layer region.

Figure 6:
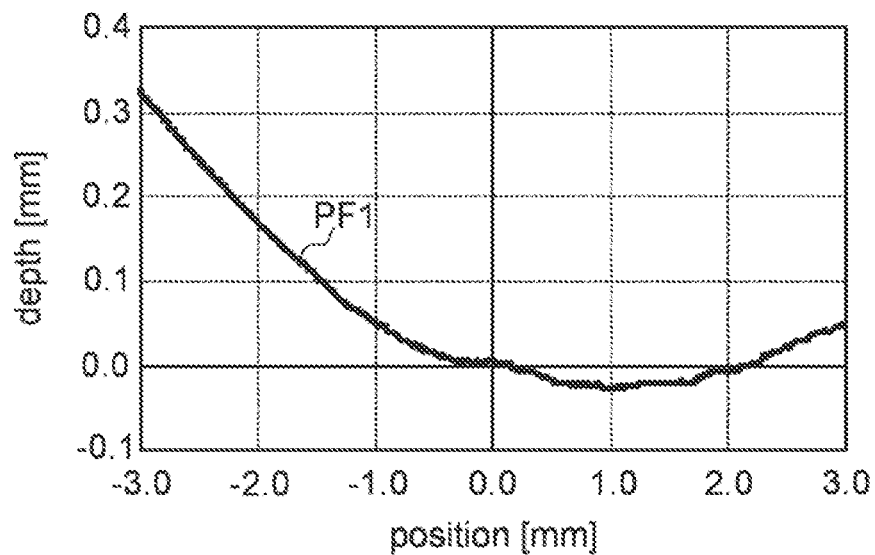
FIG. 6 is a schematic diagram for explaining an operation of the ophthalmologic apparatus according to the embodiments.
Figure 7:
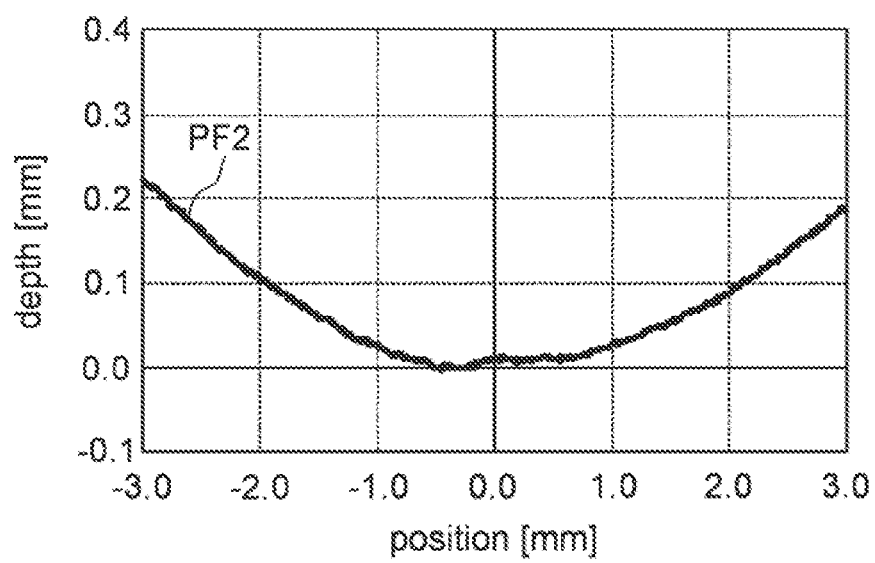
FIG. 7 is a schematic diagram for explaining an operation of the ophthalmologic apparatus according to the embodiments.

FIGS. 6 and 7 show diagrams describing the operation of the sensitivity component specifying unit 722B according to the embodiments. FIG. 6 shows an example of the shape profile obtained by performing segmentation processing by the layer region specifying unit 721. In FIGS. 6 and 7, the horizontal axis represents the variable d described above (for example, the position in the x direction, the scan position), and the vertical axis represents the depth position (for example, the position in the z direction). FIG. 7 shows an example of the shape profile obtained by the sensitivity component specifying unit 722B.

The layer region specifying unit 721 acquires the shape profile (for example, the shape profile PF1 as shown in FIG. 6) representing the shape of the predetermined layer region (for example, retinal pigment epithelium layer) by performing segmentation processing on the acquired tomographic image. The approximate processor 722A acquires the polynomial as shown as the above polynomial f(d) by performing polynomial approximation on the shape profile PF1 shown in FIG. 6. In the shape profile as shown in FIG. 6 and the polynomial f(d), an inclination component is included in the predetermined layer region due to the alignment error.

The sensitivity component specifying unit 722B extracts, as the low sensitivity component, the even order component of d (for example, the second order component of d) from the polynomial f(d), and outputs the extracted even order component as the shape profile PF2 (FIG. 7) representing the true shape of the predetermined layer region. In the shape profile PF2 shown in FIG. 7, the inclination component of the predetermined layer region is removed.

In some embodiments, the specifying unit 722 performs Legendre polynomial expansion, Fourier transform, or wavelet transform on the shape profile PF1 acquired by the layer region specifying unit 721. Even in this case, the high sensitivity component for alignment error and the low sensitivity component for alignment error can be specified. For example, the Legendre polynomials of odd orders obtained by the Legendre polynomial expansion with the component of the relative position of the measurement optical axis of the OCT unit 30 with respect to the subject's eye E with reference to the alignment reference position as a variable are high sensitivity components and the Legendre polynomials of even orders are low sensitivity components.

(Calculator 73)

The calculator 73 calculates a refractive power obtained by objectively measuring the subject's eye E, and calculates a refractive power of the peripheral region of the region including a fovea of the subject's eye E based on the calculated refractive power and the shape (shape profile) of the fundus Ef specified by the specifying unit 722. In some embodiments, the calculator 73 calculates the refractive power of the peripheral region of a region including the fovea of the subject's eye based on the calculated refractive power and a parameter representing optical characteristics of the subject's eye corresponding to the shape of the fundus specified by the specifying unit 722. The calculator 73 can build an eyeball model based on the parameter representing optical characteristics of the subject's eye corresponding to the shape of the fundus Ef specified by the specifying unit 722, and can calculate the refractive power of the above peripheral region from the built eyeball model and the calculated refractive power.

As shown in FIG. 5, the calculator 73 includes a refractive power calculator 73A, an eyeball model building unit 73B, and a peripheral refractive power calculator 73C.

(Refractive Power Calculator 73A)

The refractive power calculator 73A calculates the refractive power by processing the output from the imaging element of the light reception system of the refractometry unit 20.

In some embodiments, the refractive power calculator 73A executes a process of specifying an elliptical shape by elliptically approximating the ring pattern image acquired by the imaging element and a process of obtaining the refractive power (measurement data) based on the specified elliptical shape and a diopter for focus adjustment for the focusing lens and the like.

In some embodiments, the refractive power calculator 73A executes a process of obtaining brightness distribution in the image in which the ring pattern image acquired by the imaging element is depicted, a process of obtaining a position of the center of gravity of the ring pattern image from the obtained brightness distribution, a process of obtaining brightness distribution along a plurality of scanning directions extending radially from the obtained position of the center of gravity, a process of specifying a ring pattern image from the obtained brightness distribution along the plurality of scanning directions, a process of obtaining an approximate ellipse from the specified ring pattern image, and a process of calculating the refractive power by substituting the major axis and the minor axis of the obtained approximate ellipse into a known expression.

In some embodiments, the refractive power calculator 734 executes a process of obtaining a deflection (position shift, deformation, etc.) from the reference pattern of the ring pattern image acquired by the imaging element, and a process of obtaining the refractive power from this deflection.

In some embodiments, a spherical power S, an astigmatic power C, and an astigmatic axis angle C is calculated as the refractive power. In some embodiments, an equivalent spherical power SE (=S+C/2) is calculated as the refractive power.

(Eyeball Model Building Unit 73B)

The eyeball model building unit 73B builds an eyeball model. The eyeball model building unit 73B can build (form) a new eyeball model by applying separately acquired parameters to an eyeball model such as a known schematic eye.

The eyeball model building unit 73B can build a new eyeball model by applying an intraocular distance of the subject's eye E acquired by OCT measurement or the like as the measured parameter to an eyeball model such as a known schematic eye. In this case, the data processor 70 can execute calculation processing or the like for obtaining the size (layer thickness, volume, etc.) of the tissue or the distance between predetermined sites. For example, the data processor 70 specifies peak positions of the detection result (interference signal) of the interference light corresponding to the predetermined sites in the eye by analyzing the scan data or the tomographic image, and obtains the intraocular distance based on the distance between the specified peak positions. In some embodiments, the data processor 70 obtains the intraocular distance (distance between layers) based on the number of pixels existing between the two layer regions obtained by performing segmentation processing and a predetermined spacing correction value. The measurement of the intraocular distance is performed along a predetermined direction. The measurement direction of the intraocular distance may be, for example, a direction determined by OCT scan (for example, the traveling direction of the measurement light), or a direction determined based on scan data (for example, the direction orthogonal to the layer). Further, the distance data may be distance distribution data between the two layer regions, a statistic value (for example, average, maximum value, minimum value, median, mode, variance, standard deviation) calculated from this distance distribution data, or distance data between representative points of each layer region. Examples of the intraocular distance, which the data processor 70 can calculate, include an axial length, a corneal thickness, an anterior chamber depth, a crystalline lens thickness, a length of vitreous cavity, a retinal thickness, a choroidal thickness, and the like. Further, the data processor 70 is capable of calculating various parameters representing optical characteristics of the eyeball using the obtained intraocular distance.

In some embodiments, the specifying unit 722 (or the eyeball model building unit 73B) is capable of specifying the shape of the fundus Ef using the built eyeball model. For example, the specifying unit 722 specifies the shape of the fundus Ef by obtaining a difference between a central region of the fundus Ef and the depth position of the peripheral region.

(Peripheral Refractive Power Calculator 73C)

The peripheral refractive power calculator 73C calculates the refractive power of the peripheral region outside the region including the fovea in the fundus Ef. At this time, the peripheral refractive power calculator 73C calculates the refractive power of the peripheral region based on the refractive power of the central region acquired by the refractometry unit 20 and the specified shape of the fundus Ef. The peripheral refractive power calculator 73C is capable of calculating the refractive power of the peripheral region using the parameters of the eyeball model built by the eyeball model building unit 73B.

In some embodiments, the functions of the data processor 70 are realized by one or more processors. In some embodiments, each function of the alignment processor 71, the analyzer 72, and the calculator 73 is realized by a single processor. In some embodiments, the function of each part of the alignment processor 71 is realized by a single processor. In some embodiments, the function of the analyzer 72 is realized by a single processor. In some embodiments, the function of each part of the calculator 73 is realized by a single processor. In some embodiments, at least part of the data processor 70 is provided in the refractometry unit 20 or the OCT unit 30.

(Controller 80)

The controller 80 controls each part of the ophthalmologic apparatus 1. The controller 80 includes a storage unit (now show), and can store various types of information. Examples of the information stored in the storage unit include a program for controlling each part of the ophthalmologic apparatus 1, information of the subject, information of the subject's eye, measurement data acquired by the measurement unit 10, processing results by the data processor 70, and the like. The functions of the controller 80 is realized by a processor.

The controller 80 is capable of controlling a display device (not shown). Upon receiving control of the controller 80, the display device displays information, as a part of user interface. The display device may be, for example, a liquid crystal display (LCD), or an organic light-emitting diode (OLED) display.

The controller 80 can control the ophthalmologic apparatus 1 in accordance with a signal from an operation device (not shown). The operation device functions as a part of the user interface unit. The operation device may include various types of hardware keys (the joystick, buttons, switches, etc.) provided in the ophthalmologic apparatus 1. Further, the operation device may include various types of peripheral devices (keyboard, mouse, joystick, operation panel, etc.) connected to the ophthalmologic apparatus 1. Further, the operation device may include various kinds of software keys (buttons, icons, menus, etc.) displayed on the touch panel.

(Movement Mechanism 90)

The movement mechanism 90 is a mechanism for moving the head unit in upper and horizontal directions and front-back direction, the head unit housing the optical systems (optical systems of the apparatus) such as the refractometry unit 20, the OCT unit 30, the alignment light projection unit 40, the beam splitters BS1 and BS2, and the like. The movement mechanism 90 can relatively move the measurement unit 10 with respect to the subject's eye E under the control of the controller 80. For example, the movement mechanism 90 is provided with an actuator that generates driving force for moving the head unit and a transmission mechanism that transmits the driving force to the head unit. The actuator is configured by a pulse motor, for example. The transmission mechanism is configured by a combination of gears, a rack and pinion, and the like, for example. The main controller 80 controls the movement mechanism 90 by sending a control signal to the actuator.

The control for the movement mechanism 90 is used for position matching (alignment). For example, the controller 80 obtains a current position of the measurement unit 10 (optical system of the apparatus). The controller 80 receives information representing the content of the movement control of the movement mechanism 90, and obtains the current position of the measurement unit 10. In this case, the controller 80 controls the movement mechanism 90 at a predetermined timing (upon start-up of the apparatus, upon inputting patient information, etc.) to move the measurement unit 10 to a predetermined initial position. Thereafter, the controller 80 records the control content each time the movement mechanism 90 is controlled. Thereby, a history of the control contents can be obtained. As an optical system position obtaining unit, the controller 80 refers to this history, obtains the control contents up to the present time, and determines the current position of the measurement unit 10 based on the control contents.

In some embodiments, each time the controller 80 controls the movement mechanism 90, the controller 80 receives the control content and sequentially obtains the current position of the measurement unit 10. In some embodiments, a position sensor is provided in the ophthalmologic apparatus 1, the position sensor detecting the position of the measurement unit 10. The controller 80 obtains the current position of the measurement unit 10 based on the detection result of the position sensor.

The controller 80 can control the movement mechanism 90 based on the current position obtained as described above and the movement target position determined by the movement target position determining unit 71C. Thereby, the measurement unit 10 can be moved to the movement target position. For example, the controller 80 obtains a difference between the current position and the movement target position. The value of this difference is a vector value having the current position as a start point and the movement target position as an end point, for example. This vector value is a three-dimensional vector value expressed in the xyz coordinate system, for example.

In some embodiments, the control for the movement mechanism 90 is used for tracking. Here, tracking is to move the optical system of the apparatus according to the movement of the subject's eye E. To perform tracking, alignment and focus adjustment are performed in advance. The tracking is a function of maintaining a suitable positional relationship in which alignment and focusing are matched by causing the position of the optical system of the apparatus and the like to follow the eye movement.

The control processor 50 or the data processor 70 is an example of the "ophthalmologic information processing apparatus" according to the embodiments. The OCT unit 30 and the imaging unit 60 or the device (a communication interface, an input output interface, etc.) for receiving data from the external apparatus (external ophthalmologic apparatus) or a recording medium are (is) an example of the "acquisition unit" according to the embodiments. The OCT unit 30 and the image forming unit 60 are an example of the "OCT unit" according to the embodiments. The shape profile acquired by the layer region specifying unit 721 is an example of the "first shape data" according to the embodiments. The layer region specifying unit 721 is an example of the "tissue specifying unit" according to the embodiments. The shape profile acquired by the sensitivity component specifying unit 722B is an example of the "second shape data" according to the embodiments. The specifying unit 722 or the sensitivity component specifying unit 722B is an example of the "specifying part" according to the embodiments.

OPERATION EXAMPLE

The operation of the ophthalmologic apparatus 1 according to the present embodiment will be described.

Figure 8:
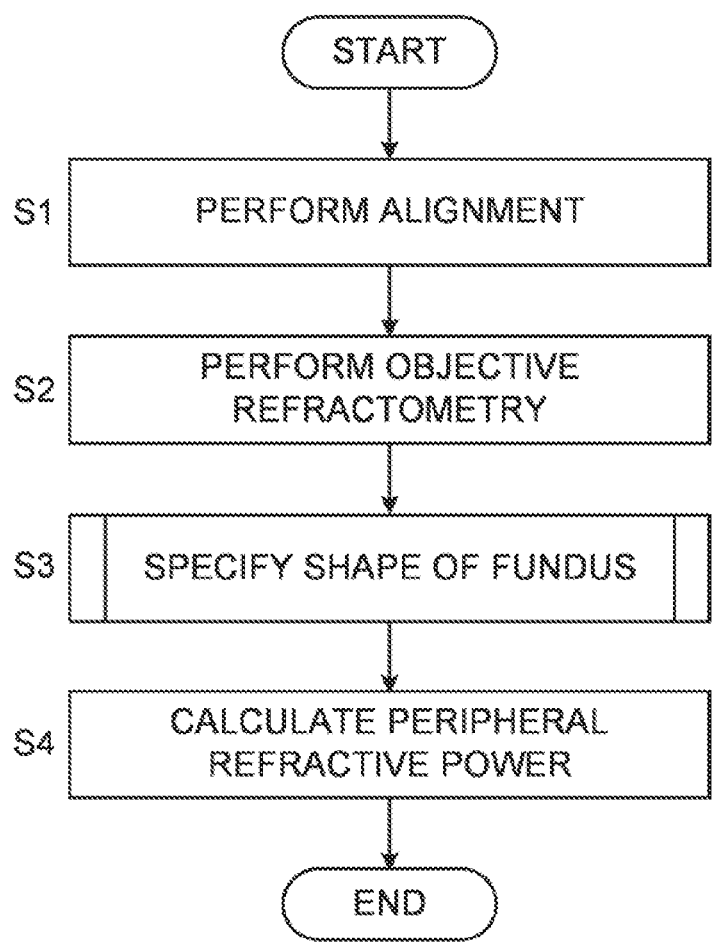
FIG. 8 is a flowchart illustrating an example of the operation of the ophthalmologic apparatus according to the embodiments.
Figure 9:
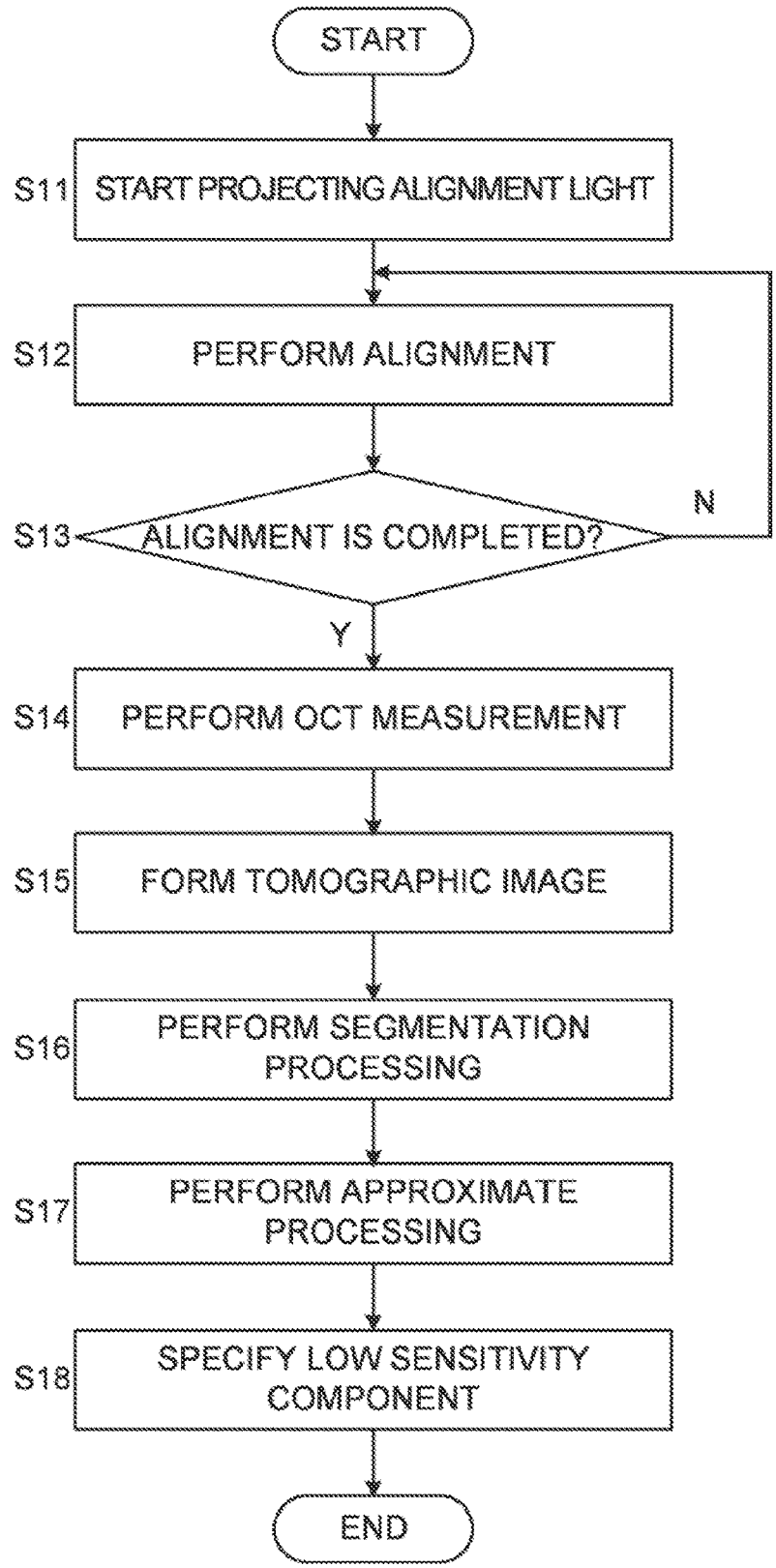
FIG. 9 is a flowchart illustrating an example of the operation of the ophthalmologic apparatus according to the embodiments.

FIGS. 8 and 9 illustrate examples of the operation of the ophthalmologic apparatus 1. FIG. 8 shows a flowchart of an example of the operation of the ophthalmologic apparatus 1. FIG. 9 shows a flowchart of an example of the operation of step S3 in FIG. 8. The storage unit of the controller 80 stores a of computer programs for realizing the processing shown in FIGS. 8 and 9. The controller 80 operates according to the computer programs, and thereby the controller 80 performs the processing shown in FIGS. 8 and 9.

(S1: Perform Alignment)

First, the controller 80 performs alignment.

For example, the controller 80 controls the alignment light projection unit 40 to project the alignment light onto the subject's eye E. At this time, a fixation light flux is projected onto the subject's eye E at a predetermined projection position (for example, a projection position on the measurement optical axis) by a fixation projection system (not shown). For example, the controller 80 specifies a movement amount and a movement direction of the measurement unit 10 from the displacement between the pupil center position and the position of the Purkinje image in the photographic image acquired by the imaging unit 100, and controls the movement mechanism 90 based on the specified movement amount and the specified movement direction to perform position matching of the measurement unit 10 with respect to the subject's eye E. The controller 80 repeatedly executes this processing until a predetermined alignment completion condition is satisfied.

(S2: Perform Objective Refractometry)

Next, the controller 80 controls the fixation projection system (not shown) to project a fixation target on the measurement optical axis of the optical system of the refractometry unit 20 in the fundus Ef (central fixation). After that, the controller 80 controls the refractometry unit 20 to perform objective refractometry in a state in which the fixation target is projected on the measurement optical axis of the optical system of the refractometry unit 20.

The refractive power calculator 73A calculates the refractive power of the central region including the fovea of the subject's eye E by analyzing the ring pattern image formed by the reflected light of the light projected onto the fundus Ef of the subject's eye E.

(S3: Specify Shape of Fundus)

Subsequently, the controller 80 performs the processing for specifying the shape of the fundus Ef of the subject's eye E. In the embodiments, the controller 80 controls the OCT unit 30 to perform OCT measurement (OCT scan) in a state in which the fixation target is projected on the measurement optical axis of the optical system of the refractometry unit 20 (OCT unit 30).

In step S3, the shape data representing the shape of the fundus Ef is acquired as described above. Details of step S3 will be described later.

(S4: Calculate Peripheral Refractive Power)

Subsequently, the controller 80 controls the peripheral refractive power calculator 73C to calculate the refractive power of the peripheral region outside the central region including the fovea obtained in step S2. Therefore, the controller 80 controls the eyeball model building unit 73B to build the eyeball model.

Specifically, the eyeball model building unit 73B obtains Height shape data [pixel] of the predetermined layer region from the data acquired in step S3. The Height data corresponds to a distance in the depth direction from a predetermined reference position in the tomographic image. The eyeball model building unit 73B obtains a distance [mm] of the Height data using pixel spacing correction value [mm/pixel] which is defined by the optical system and is specific to the apparatus. Further, the eyeball model building unit 73B builds the eyeball model using the obtained Height data as fundus shape data.

Figure 10:
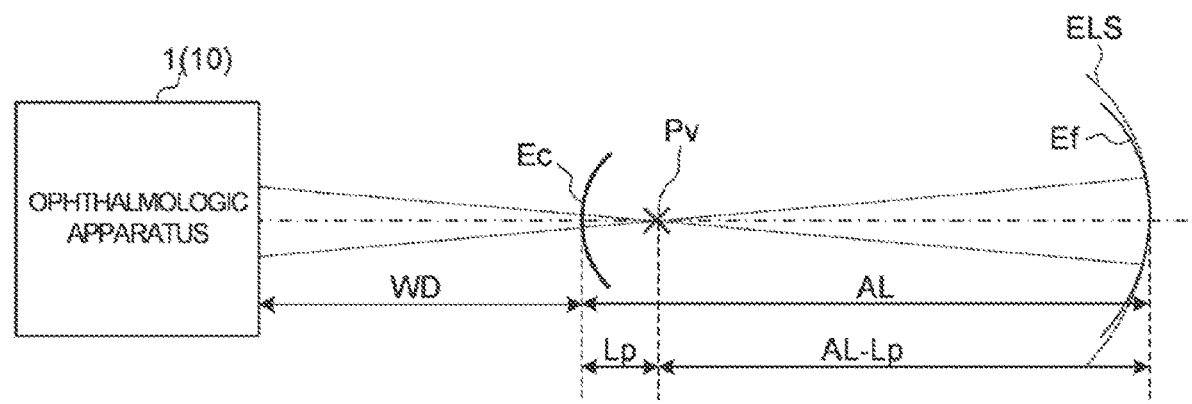
FIG. 10 is a schematic diagram for explaining an operation of the ophthalmologic apparatus according to the embodiments.

FIG. 10 shows a diagram describing the operation of the eyeball model building unit 73B according to the embodiments. FIG. IC) schematically illustrates a part of parameters of the eyeball model.

The eyeball model building unit 73B builds the eyeball model having a predetermined corneal curvature radius (for example, 7.7 mm) and a predetermined axial length (for example, 24.2 min) using parameters of an eyeball model such as Gullstrand schematic eye.

The eyeball model building unit 73B sets a pivot point Pv, which is specific to the apparatus, between the cornea Ec and the fundus Ef in the eyeball model, as shown in FIG. 10. Typically, a position corresponding to a pupil position disposed at a position optically conjugate with the optical scanner included in the scan system (for example, a position of 3 mm apart on the rear side with respect to the cornea Ec) is set as the pivot point Pv. Equidistant (equal optical path length) positions (ELS) about the pivot point Pv correspond to flat positions in the tomographic image obtained by the OCT measurement.

In the eyeball model, the axial length AL and the distance Lp from the anterior surface (posterior surface) of the cornea to the pivot point Pv are known. Therefore, the distance (AL-Lp) from the pivot point Pv to the fundus Ef is known. When the curvature radius of the fundus Ef is equal to the distance (AL-Lp), the equidistant positions correspond to the flat positions in the tomographic image as described above. Thereby, the eyeball model building unit 73B can specify the shape (for example, curvature radius) of the fundus Ef from the distance [mm] of the obtained Height data.

Therefore, the eyeball model building unit 73B obtains the difference (fundus shape difference data) $\Delta h$ [mm] of the height of the peripheral region with respect to the central region (fovea). The difference $\Delta h$ may be obtained for each A line in the tomographic image, or may be obtained by fitting with an arbitrary function such as a polynomial or an aspheric expression (polynomial including a conic constant).

Next, the peripheral refractive power calculator 73C defines a refractive power of the whole eye system in order to relate the shape of the fundus and the refractive power. In a typical eyeball model (Gullstrand schematic eye (precise schematic eye, accommodation pausing state)), the refractive power of the whole eye system is 58.64 [Diopter]. In the air conversion length, the focal length of the whole eye system is "1000/58.64=17.05" [mm]. Information on unit [mm] obtained using the pixel spacing correction value usually represents the distance in tissue of the living body. Thereby, the focal length of the whole eye system in tissue of the living body can be calculated by multiplying a refractive index. Assuming that the equivalent refractive index of the whole eye system is n=1.38, the focal length ft of the whole eye system in tissue of the living body is "1000/58.64×1.38=23.53" [mm].

The peripheral refractive power calculator 73C calculates the difference $\Delta D$ of the eyeball refractive power at the position of the difference $\Delta h$ of the height of the peripheral region with respect to the central region (fovea) according to expression (1). The difference $\Delta D$ corresponds to the difference in the eyeball refractive power relative to the central region including the fovea.

[Expression 1]

$$\Delta D = \frac{1000}{23.53 - \Delta h} - \frac{1000}{23.53} \quad (1)$$

For example, when $\Delta h$=0.1 (in tissue), $\Delta D$=0.18 [Diopter].

The peripheral refractive power calculator 73C obtains the refractive power SEp of the peripheral region by applying the difference $\Delta D$ of expression (1) to the equivalent spherical power SE of the central region, as shown in expression (2).

[Expression 2]

$$SEp = SE + \Delta D \quad (2)$$

The peripheral refractive power calculator 73C may obtain the refractive power of the peripheral region in the tomographic image for each A line, or may obtain by fitting with an arbitrary function.

In some embodiments, the peripheral refractive power calculator 73C calculates the refractive powers of each of a plurality of sites in the peripheral region of the region including the fovea of the subject's eye, and calculates statistics of the calculated plurality of refractive powers. In some embodiments, the refractive powers are refractive powers of a plurality of sites having axisymmetric relationship or point-symmetric relationship with the region including the fovea in the peripheral region. In some embodiments, the statistics is an average value of the plurality of refractive powers, a maximum value of the plurality of refractive powers, a minimum value of the plurality of refractive powers, a median value of the plurality of refractive powers, or a mode value of the plurality of refractive powers.

This terminates the operation of the ophthalmologic apparatus 1 (END).

In step S3 in FIG. 8, processing for specifying the shape of the fundus Ef of the subject's eye E is performed as shown in FIG. 9.

(S11: Start Projection Alignment Light)

When the processing of step S3 is started, the controller 80 controls the alignment light projection unit 40 to start projecting the alignment light onto the subject's eye E.

Also in step S11, in the same manner as in step S1, the fixation light flux is projected onto the subject's eye E at the predetermined projection position (for example, the projection position on the measurement optical axis) by the fixation projection system (not shown).

(S12: Perform Alignment)

The controller 80 specifies a movement amount and a movement direction of the measurement unit 10 from the displacement between the pupil center position and the position of the Purkinje image in the photographic image acquired by the imaging unit 100, and controls the movement mechanism 90 based on the specified movement amount and the specified movement direction to perform position matching of the measurement unit 10 with respect to the subject's eye E.

(S13: Alignment is Completed?)

The controller 80 determines whether the predetermined alignment completion condition is satisfied. The alignment completion condition includes that a position of the optical axis of the measurement unit 10 in the x and the y directions coincides with the movement target position in the x and the y directions, and that a distance in the z direction becomes a predetermined working distance. In some embodiments, the working distance is the working distance of the measurement unit 10 (objective lens).

When it is determined that the predetermined alignment completion condition is not satisfied (S13: N), the operation of the ophthalmologic apparatus 1 proceeds to step S12. When it is determined that the predetermined alignment completion condition is satisfied (S13: Y), the operation of the ophthalmologic apparatus 1 proceeds to step S14.

(S14: Perform OCT Measurement)

When it is determined that the predetermined alignment completion condition is satisfied (S13: Y) in step S13, the controller 80 controls the OCT unit 30 to perform OCT measurement by perform OCT scan on a predetermined site in the fundus Ef Examples of the predetermined site include the fovea, the its vicinity, and the like. Examples of the OCT scan include the radial scan, and the like.

(S15: Form Tomographic Image)

Sequentially, the controller 80 controls the image forming unit 60 to form the tomographic image of the fundus Ef based on the scan data acquired in step S14.

(S16: Perform Segmentation Processing)

Next, the controller 80 controls the layer region specifying unit 721 to specify the predetermined layer region (for example, retinal pigment epithelium layer) by performing segmentation processing on the tomographic image formed in step S15. Thereby, the shape data (shape profile) of the predetermined layer region is obtained.

(S17: Perform Approximate Processing)

Next, the controller 80 controls the approximate processor 722A to perform approximate processing on the shape data obtained in step S16. The approximate processor 722A obtains the polynomial (for example, the above polynomial f(d)) by performing polynomial approximation on the shape data, for example.

(S18: Specify Low Sensitivity Component)

The controller 80 controls the sensitivity component specifying unit 722B to specify the low sensitivity component from the polynomial obtained in step S17. The sensitivity component specifying unit 722B specifies, for example, the even order component of d (for example, the second order component of d) from the polynomial f(d) as the low sensitivity component, and outputs the specified low sensitivity component as the shape profile representing the true shape of the predetermined layer region. In step S4 in FIG. 8, the profile output in step S18 is used as the data representing the shape of the predetermined layer region (for example, retinal pigment epithelium layer) corresponding to the shape of the fundus Ef.

This terminates the processing of step S3 in FIG. 8 (END).

MODIFICATION EXAMPLE

The configuration and the operation of the ophthalmologic apparatus according to the embodiments are not limited to the above embodiments. [First Modification Example]

In step S4, the eyeball model building unit 73B may build a new eyeball model by replacing at least one of the measured data (for example, measured values of axial length, cornea shape, anterior chamber depth, curvature of crystalline lens, thickness of crystalline lens) among the parameters of the eyeball model such as the Gullstrand schematic eye. In some embodiments, the measured data is obtained from the external measurement apparatus or the electronic health record system. In some embodiments, the axial length, the anterior chamber depth, the curvature of crystalline lens, and the thickness of crystalline lens are obtained from the scan data acquired by the OCT unit 30.

For example, the peripheral refractive power calculator 73C (or the data processor 70) performs ray tracing processing on a ray incident from the cornea Ec, passing through the pupil, and reaching the fundus Ef, using the built new eyeball model (for example, pupil diameter=φ4). In the ray tracing processing, a position of the object point is set to a position corresponding to a far point obtained from the refractive power (equivalent spherical power SE) in the central region acquired in step S2. The far distance L from the cornea Ec to the position corresponding to the far point is "−1000/SE" [mm].

First, the peripheral refractive power calculator 73C performs the ray tracing processing for the central region. The measured data is applied to the eyeball model as described above. Therefore, even in the central region, the ray may not converge at the fundus Ef. In this case, the peripheral refractive power calculator 73C finely adjusts the parameters of the eyeball model so that the ray converges in the central region (the surface of the fundus Ef is the best image surface).

Next, the peripheral refractive power calculator 73C performs the ray tracing processing for the peripheral region using the eyeball model whose parameters are finely adjusted (that is, rays having incident angles with respect to the measurement optical axis passing through a rotational point of the eye are traced). The peripheral refractive power calculator 73C obtains the distance to the object point such that the rays converge on the fundus Ef in the peripheral region, by performing ray tracing processing while changing the distance to the object point. The obtained distance to the object point corresponds to the far point distance Lp in the peripheral region. The peripheral refractive power calculator 73C can obtain the refractive power SEp [Diopter] of the peripheral region using expression (3).

[Expression 3]

$$SEp = -\frac{1000}{Lp} \quad (3)$$

The peripheral refractive power calculator 73C performs ray tracing processing while changing the incident angle in a predetermined incident angle range, and obtains the refractive power SEp of the peripheral region for each incident angle (angle of view). The refractive power in the peripheral region may be a discrete value for each incident angle or may be fitted with an arbitrary function in the incident angle range.

In the present modification examples, the eyeball model is finely adjusted so that the rays converge at the fundus Ef in the central region. Therefore, the obtained refractive power of the peripheral region corresponds to obtaining a relative refractive power with respect to the central region.

SECOND MODIFICATION EXAMPLE

In the above embodiments, a tilt angle of the predetermined layer region (for example, retinal pigment epithelium layer, OS-RPE boundary surface) of the fundus with respect to the horizontal direction (a predetermined reference direction) may be specified from the above shape data or the tomographic image, as the shape of the central region of the fundus Ef.

The configuration of the ophthalmologic apparatus according to the second modification example is the same as the configuration of the ophthalmologic apparatus 1 according to the embodiments except that the eyeball model building unit 73B is omitted. Therefore, the explanation thereof is omitted.

In the present modification example, in step S3, the specifying unit 722 (or the peripheral refractive power calculator 73C) calculates a tilt angle θh of the fundus plane for the tomographic image (B scan image) in the horizontal direction and a tilt angle θv of the fundus plane for the B scan image in the vertical direction, using the Height data obtained from the tomographic image acquired in step S15.

The tilt angles θh and θv can be calculated using the same method as a tilt angle g1 as follows.

Figure 11:
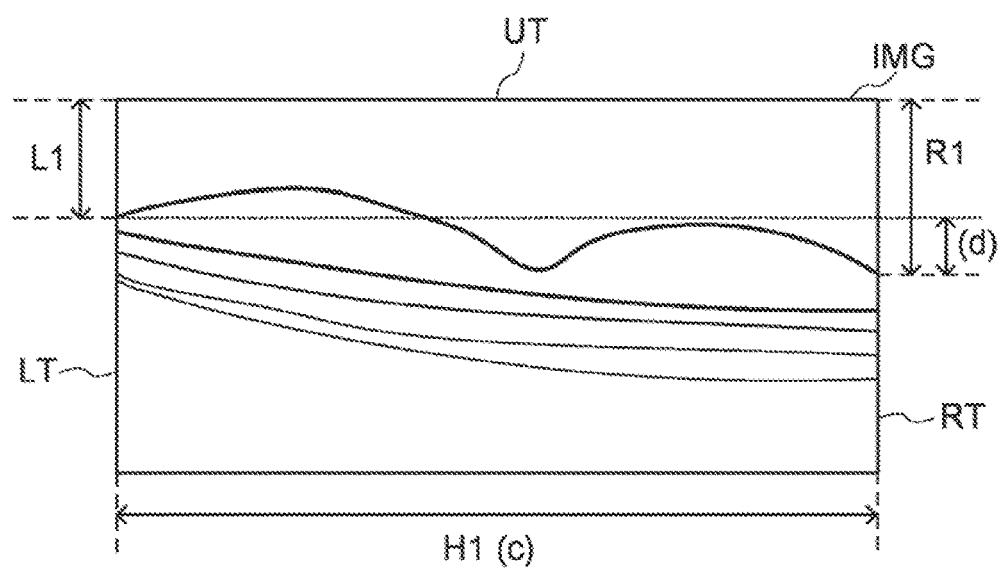
FIG. 11 is a schematic diagram for explaining an operation of the ophthalmologic apparatus according to a modification example of the embodiments.

FIG. 11 schematically shows the tomographic image in the horizontal direction.

In FIG. 11, at the left end LT of the frame of the tomographic image IMG, the distance in the vertical direction from the upper end UT of the frame to the image region of the site corresponding to the predetermined layer region (layer region specified by the layer region specifying unit 721, for example, retinal pigment epithelium layer, OS-RPE boundary surface, or the nerve fiber layer) in the fundus Ef is set as L1. In the same manner, at the right end RT of the frame of the tomographic image IMG, the distance in the vertical direction from the upper end UT of the frame to the image region of the site corresponding to the layer region is set as R1. The distance L1 is obtained using the Height data at the left end LT of the frame. The distance R1 is obtained using the Height data at the right end RT of the frame. The specifying unit 722 obtains a value d corresponding to the actual dimension for the difference (|R1-L1|) in the vertical direction of the image region of the site at the left end LT of the frame and the right end RT of the frame in the tomographic image IMG.

Next, the specifying unit 722 obtains a value c corresponding to the actual dimension for the distance H1 in the horizontal direction of the frame of the tomographic image IMG which corresponds to the OCT measurement range. For example, the value c is specified using the pixel spacing correction value [mm/pixel] for the length of scanning range in the horizontal direction.

The specifying unit 722 obtains an inclination angle g0 [degree] according to expression (4).

[Expression 4]

$$g0 = \arctan\left(\frac{|d|}{c}\right) \quad (4)$$

In some embodiments, the specifying unit 722 obtains the tilt angle of the fundus plane by correcting the inclination angle g0 according to a misalignment amount between the measurement optical axis and the eyeball optical axis.

(In the Case that the Measurement Optical Axis and the Eyeball Optical Axis Substantially Coincide with Each Other)

When the measurement optical axis and the eyeball optical axis (visual axis) substantially coincide with each other, the specifying unit 722 outputs, as the tilt angle g1 of the fundus plane, the inclination angle g0 of the tomographic image without correcting the inclination angle g0 as shown in expression (5)

[Expression 5]

$$g1 = g0 = \arctan\left(\frac{|d|}{c}\right) \quad (5)$$

(In the Case that the Eyeball Optical Axis is Shifted with Respect to the Measurement Optical Axis)

When the eyeball optical axis is shifted with respect to the measurement optical axis, the specifying unit 722 obtains the tilt angle g1 of the fundus plane by correcting the inclination angle g0 of the tomographic image based on a shift amount.

For example, the specifying unit 722 obtains a correction angle φ1 according to a linear expression with the shift amount ds as variable shown in expression (6), and then obtains the tilt angle g1 of the fundus plane by correcting the inclination angle g0 using the obtained correction angle φ1 as shown in expression (7). In expression (6), α1 and c1 are constants. For example, α1 and c1 can be obtained using the schematic eye data.

[Expression 8]

$$\varphi1 = \alpha1 \times ds + c1 \quad (6)$$

[Expression 7]

$$g1 = g0 - \varphi1 \quad (7)$$

(In the Case that the Eyeball Optical Axis is Tilted with Respect to the Measurement Optical Axis)

When the eyeball optical axis is tilted with respect to the measurement optical axis, the specifying unit 722 obtains the tilt angle g1 of the fundus plane by correcting the inclination angle g0 of the tomographic image based on a tilt amount.

For example, the specifying unit 722 obtains a correction angle φ2 according to a linear expression with the tilt amount dt as variable shown in expression (8), and then obtains the tilt angle g1 of the fundus plane by correcting the inclination angle g0 using the obtained correction angle φ2 as shown in expression (9). In expression (8), α2 and c2 are constants. For example, α2 and c2 can be obtained by using the schematic eye data.

[Expression 8]

$$\varphi2 = \alpha2 \times dt + c2 \quad (8)$$

[Expression 9]

$$g1 = g0 - \varphi2 \quad (9)$$

(In the Case that the Eyeball Optical Axis is Shifted and Tilted with Respect to the Measurement Optical Axis)

When the eyeball optical axis is shifted and tilted with respect to the measurement optical axis, the specifying unit 722 obtains the tilt angle g1 of the fundus plane by correcting the inclination angle g0 of the B scan image based on the shift amount and the tilt amount.

For example, in a range where the shift amount ds and the tilt amount dt are small, the specifying unit 722 obtains a correction angle φ3 according to an expression with the shift amount ds and the tilt amount dt as variables shown in expression (10), and then obtains the tilt angle g1 of the fundus plane by correcting the inclination angle g0 using the obtained correction angle φ3 as shown in expression (11). In some embodiments, expression (10) is a combining expression obtained by linearly combined an expression for obtaining the correction angle of the shift amount and an expression for obtaining the correction angle of the tilt amount. In expression (10), α3, α4 and c3 are constants. For example, α3, α4, and c3 can be obtained using the schematic eye data.

[Expression 10]

$$\varphi3 = \alpha3 \times ds + \alpha4 \times dt + c3 \quad (10)$$

[Expression 11]

$$g1 = g0 - \varphi3 \quad (11)$$

In the present modification example, for horizontal and vertical directions respectively, the refractive power calculator 73A corrects the ring pattern image obtained in step S2 in accordance with the tilt angles θh and θv of the fundus plane specified as described above. The refractive power calculator 73A performs ellipse approximation on the corrected ring pattern image, and obtains the refractive power using the obtained elliptical shape by a known method. The obtained refractive power is calculated as the refractive power of the central region.

For example, a major axis of the ring pattern image is LA, and a minor axis of the ring pattern image is LB, the ring pattern image being acquired when the tilt angle of the fundus plane is 0 degree. When the fundus plane is tilted in the major axis direction and the tilt angle is θ degree, the major axis of the ellipse approximated from the acquired ring pattern image is LA/cos θ, and the minor axis is LB. Therefore, the refractive power calculator 73A can correct the ring pattern image by multiplying cos θ in the major axis direction of the ellipse obtained by approximating the ring pattern image acquired in step S2. The same applies to the case of tilting in the minor axis direction. For example, the refractive power calculator 734 can correct the ring pattern image by obtaining the tilt angle in the major axis direction of the ellipse and the tilt angle in the minor axis direction of the ellipse from each of the tilt angles in the horizontal and vertical directions.

In the same manner as the above embodiments, the peripheral refractive power calculator 73C obtains the refractive power SEp of the peripheral region by applying the difference ΔD of expression (1) to the equivalent spherical power SE of the central region, as shown in expression (2).

THIRD MODIFICATION EXAMPLE

In the above embodiments or the modification examples thereof, the case has been described where the low sensitivity component for alignment error is extracted from the shape data (shape profile) obtained by the approximate processor 722A. However, the configuration of the ophthalmologic apparatus 1 according to the embodiments is not limited to this. For example, the high sensitivity component for alignment error may be extracted (separated) from the shape data, and new shape data may be acquired by removing the extracted high sensitivity component from the shape data, as the shape data representing the true shape of the predetermined layer region.

In the following, the ophthalmologic apparatus according to the third modification example will be described focusing on differences from the ophthalmologic apparatus 1 according to the embodiments.

In the third modification example, the sensitivity component specifying unit 722B specifies the high sensitivity component from the expression representing the shape profile obtained by approximate processing by the approximate processor 722A, and generates the new shape profile from which the high sensitivity component has been removed, from the expression representing the shape profile, as the shape profile representing the true shape of the predetermined layer region.

For example, in the cased that the polynomial f(d) described above is obtained by the approximate processor 722A, the sensitivity component specifying unit 722B specifies the odd order component of d (for example, the first order component of d or the third order component of d) as the high sensitivity component, and outputs the shape profile representing the true shape of the predetermined layer region obtained by subtracting the specified high sensitivity component from the above polynomial f(d).

In the third modification example, in step S3 in FIG. 8, processing for specifying the shape of the fundus Ef of the subject's eye E is performed as follow.

Figure 12:
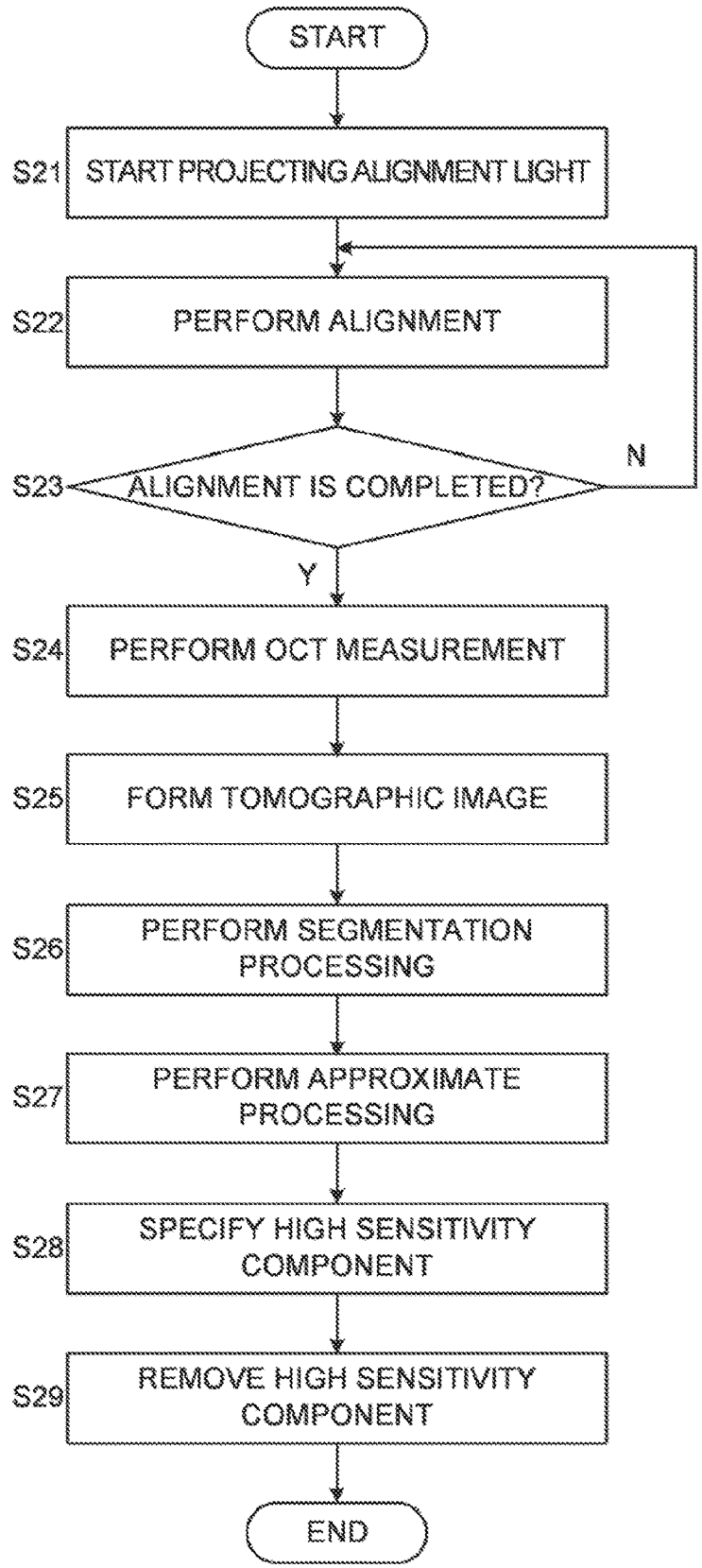
FIG. 12 is a flowchart illustrating an example of the operation of the ophthalmologic apparatus according to a modification example of the embodiments.

FIG. 12 shows an example of the operation of the ophthalmologic apparatus according to the third modification example of the embodiments. FIG. 12 shows a flowchart of an example of the operation of step S3 in FIG. 8. The storage unit of the controller 80 stores a of computer programs for realizing the processing shown in FIG. 12. The controller 80 operates according to the computer programs, and thereby the controller 80 performs the processing shown in FIG. 12.

(S21: Start Projection Alignment Light)

When the processing of step S3 is started, the controller 80 controls the alignment light projection unit 40 to start projecting the alignment light onto the subject's eye E in the same manner as in step S11.

(S22: Perform Alignment)

The controller 80 controls the movement mechanism 90 to perform position matching of the measurement unit 10 with respect to the subject's eye E in the same manner as in step S12.

(S23: Alignment is Completed?)

The controller 80 determines whether the predetermined alignment completion condition is satisfied in the same manner as in step S13.

When it is determined that the predetermined alignment completion condition is not satisfied (S23: N), the operation of the ophthalmologic apparatus 1 proceeds to step S22. When it is determined that the predetermined alignment completion condition is satisfied (S23: Y), the Operation of the Ophthalmologic Apparatus 1 Proceeds to Step S24.

(S24: Perform OCT Measurement)

When it is determined that the predetermined alignment completion condition is satisfied (S23: Y), the controller 80 controls the OCT unit 30 to perform OCT scan on a predetermined site in the fundus Ef to perform OCT measurement in the same manner as in step S13.

(S25: Form Tomographic Image)

Sequentially, the controller 80 controls the image forming unit 60 to form the tomographic image of the subject's eye E based on the scan data obtained in step S24, in the same manner as step S15.

(S26: Perform Segmentation Processing)

Next, the controller 80 controls the layer region specifying unit 721 to specify the predetermined layer region (for example, retinal pigment epithelium layer) by performing segmentation processing on the tomographic image formed in step S25, in the same manner as step S16.

(S27: Perform Approximate Processing)

Next, the controller 80 controls the approximate processor 722A to perform approximate processing on the shape data obtained in step S26, in the same manner as in step S17.

(S28: Specify High Sensitivity Component)

The controller 80 controls the sensitivity component specifying unit 722B to specify the high sensitivity component from the polynomial obtained in step S27. The sensitivity component specifying unit 722B specifies, for example, the odd order component of d (for example, the first order component of d or the third order component of d) from the polynomial f(d) as the high sensitivity component.

(S29: Remove High Sensitivity Component)

The controller 80 controls the sensitivity component specifying unit 722B so as to remove the high sensitivity component specified in step S28 from the shape data obtained in step S27. The sensitivity component specifying unit 722B generates the shape profile representing the true shape of the predetermined layer region by subtracting the high sensitivity component from the polynomial f(d) obtained by approximate processing in step S27. In step S4 in FIG. 8, the profile output in step S29 is used as the data representing the shape of the predetermined layer region (for example, retinal pigment epithelium layer) corresponding to the shape of the fundus Ef.

This terminates the processing of step S3 in FIG. 8 (END).

[Fourth Modification]

In the above embodiments or the modification examples thereof, the case has been described where the low sensitivity component or the high sensitivity component for alignment error is specified by performing polynomial approximation on the shape profile by approximate processor 722A. However, the configuration of the ophthalmologic apparatus 1 according to the embodiments is not limited to this. For example, the low sensitivity component for alignment error may be specified from a position of a circle and a size of the circle, the circle being obtained by performing circle fitting processing on the shape profile obtained by the layer region specifying unit 721. In some embodiments, the low sensitivity component for alignment error is specified from a position of an ellipse or an aspheric surface and a size of the ellipse or the aspheric surface, the ellipse or the aspheric surface being obtained by performing elliptical fitting processing or aspheric fitting processing on the shape profile obtained by the layer region specifying unit 721. For example, an aspheric expression using a conic constant is used for the aspheric fitting processing.

In the following, the ophthalmologic apparatus according to the fourth modification example will be described focusing on differences from the ophthalmologic apparatus 1 according to the embodiments.

In the fourth modification example, the specifying unit 722 specifies one or more circles (or a part of the circumference) in which at least a part of the circumference follows the shape of the predetermined layer region, by performing known circle fitting processing on the shape profile obtained by performing segmentation processing by the layer region specifying unit 721. The specifying unit 722 is capable of specifying, as the low sensitivity component for alignment error, components representing positions of the specified one or more circles and components representing sizes of the circles. Examples of the positions of the one or more circles include center positions, curvature center positions, and the like. Examples of the sizes of the one or more circles include radii, curvatures, and the like.

For example, for each predetermined range of the shape profile, the specifying unit 722 specifies an approximate circle of the range by performing known circle fitting processing using the least-square method and the partial differential with the center position of the circle and the radius of the circle as unknowns. The approximate circle is specified using the center position and the radius. The specifying unit 722 is capable of specifying two or more approximate circles within a desired range of the shape profile by repeating the above circle fitting processing. The specifying unit 722 generates the shape profile representing the true shape of the predetermined layer region using the center positions and the radii of the specified two or more approximate circles.

In the fourth modification example, in step S3 in FIG. 8, processing for specifying the shape of the fundus Ef of the subject's eye E is performed as follow.

Figure 13:
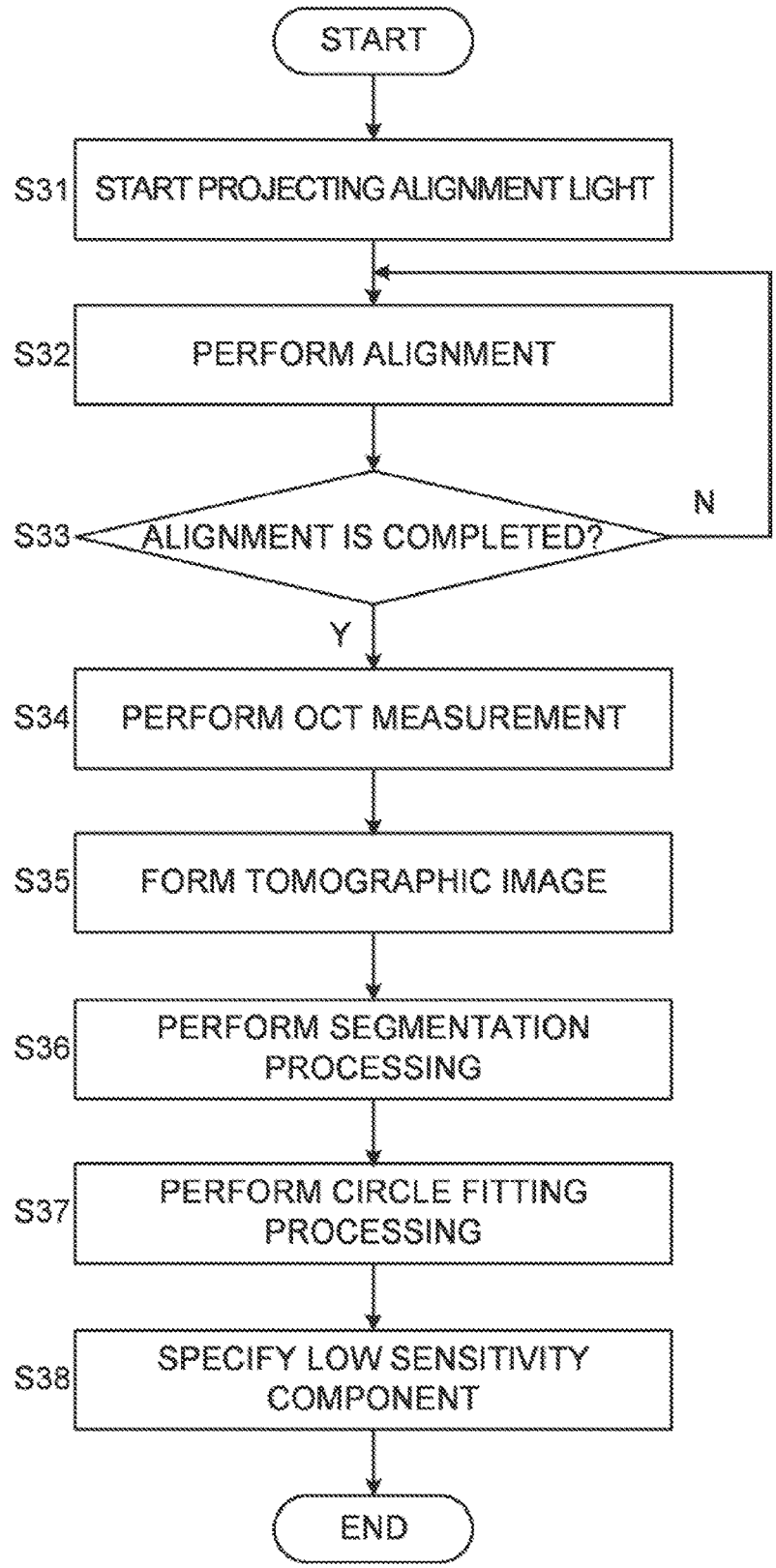
FIG. 13 is a flowchart illustrating an example of the operation of the ophthalmologic apparatus according to a modification example of the embodiments.

FIG. 13 shows an example of the operation of the ophthalmologic apparatus according to the fourth modification example of the embodiments. FIG. 13 shows a flowchart of an example of the operation of step S3 in FIG. 8. The storage unit of the controller 80 stores a of computer programs for realizing the processing shown in FIG. 13. The controller 80 operates according to the computer programs, and thereby the controller 80 performs the processing shown in FIG. 13.

(S31: Start Projection Alignment Light)

When the processing of step S3 is started, the controller 80 controls the alignment light projection unit 40 to start projecting the alignment light onto the subject's eye E in the same manner as in step S11.

(S32: Perform Alignment)

The controller 80 controls the movement mechanism 90 to perform position matching of the measurement unit 10 with respect to the subject's eye E in the same manner as in step S12.

(S33: Alignment is Completed?)

The controller 80 determines whether the predetermined alignment completion condition is satisfied in the same manner as in step S13.

When it is determined that the predetermined alignment completion condition is not satisfied (S33: N), the operation of the ophthalmologic apparatus 1 proceeds to step S32. When it is determined that the predetermined alignment completion condition is satisfied (S33: Y), the operation of the ophthalmologic apparatus 1 proceeds to step S34.

(S34: Perform OCT Measurement)

When it is determined that the predetermined alignment completion condition is satisfied (S33: Y), the controller 80 controls the OCT unit 30 to perform OCT scan on a predetermined site in the fundus Ef to perform OCT measurement in the same manner as in step 13.

(S35: Form Tomographic Image)

Sequentially, the controller 80 controls the image forming unit 60 to form the tomographic image of the subject's eye E based on the scan data obtained in step S34, in the same manner as step S15.

(S36: Perform Segmentation Processing)

Next, the controller 80 controls the layer region specifying unit 721 to specify the predetermined layer region (for example, retinal pigment epithelium layer) by performing segmentation processing on the tomographic image formed in step S35, in the same manner as step S16.

(S37: Perform Circle Fitting Processing)

Next, the controller 80 controls the specifying unit 722 to perform known circle fitting processing on the shape data obtained in step S36. In some embodiments, the controller 80 controls the specifying unit 722 to perform circle fitting processing on corrected shape data in which the optical distortion of the shape data obtained in step S36 is corrected. For example, the specifying unit 722 can obtain the corrected shape data by converting the shape data in the OCT coordinate system obtained in step S36 into the shape data of the real space coordinate system. The specifying unit 722 specifies, as described above, the one or more approximate circles corresponding to the shape data (or the corrected shape data), and generates the shape profile representing the true shape of the predetermined layer region using the center positions and the curvatures of the specified one or more approximate circles. In step S4 in FIG. 8, the profile output in step S37 is used as the data representing the shape of the predetermined layer region (for example, retinal pigment epithelium layer) corresponding to the shape of fundus Ef.

This terminates the processing of step S3 in FIG. 8 (END).

[Effects]

The ophthalmologic apparatus and the method of controlling the ophthalmologic apparatus according to the embodiments are explained.

An ophthalmologic information processing apparatus (control processor 50, or data processor 70) according to some embodiments includes an acquisition unit (OCT unit 30 and image forming unit 60, or a device ((communication interface, input/output interface, etc.) that receives data from an external apparatus (external ophthalmologic apparatus) or a recording medium), a tissue specifying unit (layer region specifying unit 721), and a specifying unit (722). The acquisition unit is configured to acquire a tomographic image of a subject's eye (E) formed based on scan data acquired using an optical system (OCT unit 30) for performing optical coherence tomography on the subject's eye. The tissue specifying unit is configured to acquire first shape data (shape profile) representing shape of a tissue of the subject's eye by performing segmentation processing on the tomographic image. The specifying unit is configured to specify a low sensitivity component having a small variation with respect to a change in a position of the optical system with respect to the subject's eye from the first shape data, and to obtain second shape data (shape profile) representing shape of the tissue based on the specified low sensitivity component.

According to such a configuration, the low sensitivity component for the displacement of the relative position between the subject's eye and the optical system is specified from the shape data representing the shape of the tissue of the subject's eye, and the new shape data is generated from the low sensitivity component of the shape data Thereby, the influence of the displacement between the subject's eye and the optical system for measuring the shape of the tissue can be reduced, and the shape of the tissue of the subject's eye can be specified with high reproducibility and high accuracy.

In some embodiments, the specifying unit specifies, as the low sensitivity component, a symmetric component of the position of the optical system with respect to the subject's eye, with reference to an alignment reference position of the optical system with respect to the subject's eye.

According to such a configuration, the new shape data is generated by specifying the symmetric component of the position of the optical system with respect to the alignment reference position from the shape data Thereby, the influence of the displacement between the subject's eye and the optical system for measuring the shape of the tissue can be reduced with simple processing, and the shape of the tissue of the subject's eye can be specified with high reproducibility and high accuracy.

In some embodiments, the specifying unit specifies, as the low sensitivity component, an even order component of the position of the optical system among a polynomial obtained by performing polynomial approximation on the first shape data.

According to such a configuration, with simple processing using the polynomial approximation processing, the influence of the displacement between the subject's eye and the optical system for measuring the shape of the tissue can be reduced, and the shape of the tissue of the subject's eye can be specified with high reproducibility and high accuracy.

In some embodiments, the low sensitivity component includes a component representing a curvature of the tissue.

According to such a configuration, the tissue of the subject's eye is specified using the curvature. Thereby, the influence of the displacement between the subject's eye and the optical system for measuring the shape of the tissue can be reduced, and the shape of the tissue of the subject's eye can be specified with high reproducibility and high accuracy.

In some embodiments, the specifying unit specifies, as the low sensitivity component, a component representing a position of a circle, which is obtained by performing circle fitting processing on the first shape data, and a component representing a size of the circle.

According to such a configuration, the tissue of the subject's eye is specified based on the position of the circle and the size of the circle, the circle being obtained by performing circle fitting processing. Thereby, the influence of the displacement between the subject's eye and the optical system for measuring the shape of the tissue can be reduced, and the shape of the tissue of the subject's eye can be specified with high reproducibility and high accuracy.

An ophthalmologic information processing apparatus (control processor 50, or data processor 70) according to some embodiments includes an acquisition unit (OCT unit 30 and image forming unit 60, or a device ((communication interface, input/output interface, etc.) that receives data from an external apparatus (external ophthalmologic apparatus) or a recording medium), a tissue specifying unit (layer region specifying unit 721), and a specifying unit (722). The acquisition unit is configured to acquire a tomographic image of a subject's eye (E) formed based on scan data acquired using an optical system (OCT unit 30) for performing optical coherence tomography on the subject's eye. The tissue specifying unit is configured to acquire first shape data representing shape of a tissue of the subject's eye by performing segmentation processing on the tomographic image. The specifying unit is configured to specify a high sensitivity component having a large variation with respect to a change in a position of the optical system with respect to the subject's eye from the first shape data, and to obtain second shape data representing shape of the tissue by removing the specified high sensitivity component from the first shape data.

According to such a configuration, the high sensitivity component for the displacement of the relative position between the subject's eye and the optical system is specified from the shape data representing the shape of the tissue of the subject's eye, and the new shape data is generated by removing the high sensitivity component from the shape data. Thereby, the influence of the displacement between the subject's eye and the optical system for measuring the shape of the tissue can be reduced, and the shape of the tissue of the subject's eye can be specified with high reproducibility and high accuracy.

In some embodiments, the specifying unit specifies, as the high sensitivity component, an asymmetric component of the position of the optical system with respect to the subject's eye, with reference to an alignment reference position of the optical system with respect to the subject's eye.

According to such a configuration, the new shape data is generated by specifying the asymmetric component of the position of the optical system with respect to the alignment reference position from the shape data and removing the asymmetric component from the shape data Thereby, the influence of the displacement between the subject's eye and the optical system for measuring the shape of the tissue can be reduced with simple processing, and the shape of the tissue of the subject's eye can be specified with high reproducibility and high accuracy.

In some embodiments, the specifying unit specifies, as the high sensitivity component, an odd order component of the position of the optical system among a polynomial obtained by performing polynomial approximation on the first shape data.

According to such a configuration, with simple processing using the polynomial approximation processing, the influence of the displacement between the subject's eye and the optical system for measuring the shape of the tissue can be reduced, and the shape of the tissue of the subject's eye can be specified with high reproducibility and high accuracy.

In some embodiments, the high sensitivity component includes a component representing an inclination of the tissue with respect to a predetermined reference direction.

According to such a configuration, the tissue of the subject's eye is specified based on the inclination of the tissue. Thereby, the influence of the displacement between the subject's eye and the optical system for measuring the shape of the tissue can be reduced, and the shape of the tissue of the subject's eye can be specified with high reproducibility and high accuracy.

In some embodiments, the tissue includes a predetermined layer region (for example, retinal pigment epithelium layer) in a fundus (Ef).

According to such a configuration, the shape of the fundus can be specified with high reproducibility and high accuracy, without being affected by the displacement between the subject's eye and the optical system.

Some embodiments further include a calculator (peripheral refractive power calculator 73C) that calculates a refractive power of a peripheral region of a region including a fovea of the subject's eye based on a refractive power obtained by objectively measuring the subject's eye and parameter representing optical characteristics of the subject's eye corresponding to the shape of the tissue on the basis of the second shape data acquired by the specifying unit.

According such a configuration, in accordance with the shape of the fundus of the subject's eye, the refractive power of the peripheral region of the region including the fovea can be obtained with high accuracy.

In some embodiments, the shape of the tissue includes a tilt angle of the tissue with respect to a predetermined reference direction.

According to such a configuration, in accordance with the tilt angle of the predetermined layer region in the fundus with respect to the predetermined reference direction, the refractive power of the peripheral region of the region including the fovea can be obtained with high accuracy.

An ophthalmologic apparatus (1) according to some embodiments include the optical system (optical system included in the OCT unit 30), a movement mechanism (90) that moves the subject's eye and the optical system relative to each other, and the ophthalmologic information processing apparatus described any one of the above.

According to such a configuration, the ophthalmologic apparatus, which is capable of reducing the influence of the displacement between the subject's eye and the optical system for measuring the shape of the tissue, and of specifying the shape of the tissue of the subject's eye with high reproducibility and high accuracy, can be provided.

An ophthalmologic information processing method includes an acquisition step, a tissue specifying step, and a specifying step. The acquisition step acquires a tomographic image of a subject's eye (E) formed based on scan data acquired using an optical system (OCT unit 30) for performing optical coherence tomography on the subject's eye. The tissue specifying step acquires first shape data representing shape of a tissue of the subject's eye by performing segmentation processing on the tomographic image. The specifying step specifies a low sensitivity component having a small variation with respect to a change in a position of the optical system with respect to the subject's eye from the first shape data, and obtains second shape data representing shape of the tissue based on the specified tow sensitivity component.

According to such a method, the low sensitivity component for the displacement of the relative position between the subject's eye and the optical system is specified from the shape data representing the shape of the tissue of the subject's eye, and the new shape data is generated from the low sensitivity component of the shape data. Thereby, the influence of the displacement between the subject's eye and the optical system for measuring the shape of the tissue can be reduced, and the shape of the tissue of the subject's eye can be specified with high reproducibility and high accuracy.

An ophthalmologic information processing method includes an acquisition step, a tissue specifying step, and a specifying step. The acquisition step acquires a tomographic image of a subject's eye (E) formed based on scan data acquired using an optical system (OCT unit 30) for performing optical coherence tomography on the subject's eye. The tissue specifying step acquires first shape data representing shape of a tissue of the subject's eye by performing segmentation processing on the tomographic image. The specifying step specifies a high sensitivity component having a large variation with respect to a change in a position of the optical system with respect to the subject's eye from the first shape data, and obtains second shape data representing shape of the tissue by removing the specified high sensitivity component from the first shape data.

According to such a method, the high sensitivity component for the displacement of the relative position between the subject's eye and the optical system is specified from the shape data representing the shape of the tissue of the subject's eye, and the new shape data is generated by removing the high sensitivity component from the shape data Thereby, the influence of the displacement between the subject's eye and the optical system for measuring the shape of the tissue can be reduced, and the shape of the tissue of the subject's eye can be specified with high reproducibility and high accuracy.

Some embodiments further include a calculation step that calculates a refractive power of a peripheral region of a region including a fovea of the subject's eye based on a refractive power obtained by objectively measuring the subject's eye and parameter representing optical characteristics of the subject's eye corresponding to the shape of the tissue on the basis of the second shape data acquired in the specifying step.

According such a method, in accordance with the shape of the fundus of the subject's eye, the refractive power of the peripheral region of the region including the fovea can be obtained with high accuracy.

A program according to some embodiments causes the computer to execute each step of the ophthalmologic information processing method described in any of the above.

According to such a program, the low sensitivity component or the high sensitivity component for the displacement of the relative position between the subject's eye and the optical system is specified from the shape data representing the shape of the tissue of the subject's eye, and the new shape data is generated so as to reduce the influence of the displacement of the relative position. Thereby, the influence of the displacement between the subject's eye and the optical system for measuring the shape of the tissue can be reduced, and the shape of the tissue of the subject's eye can be specified with high reproducibility and high accuracy.

<Others>

The above-described embodiments are merely examples for carrying out the present invention. Those who intend to implement the present invention can apply any modification, omission, addition, or the like within the scope of the gist of the present invention.

In some embodiments, a program for causing a computer to execute not only the ophthalmologic information processing method described above but also a method of controlling the ophthalmologic apparatus is provided. Such a program can be stored in any kind of recording medium that can be read by the computer. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic information processing apparatus comprising:
    an acquisition unit configured to acquire a tomographic image of a subject's eye formed based on scan data acquired using an optical system for performing optical coherence tomography on the subject's eye;
    processing circuitry configured to acquire first shape data representing shape of a tissue of the subject's eye by performing segmentation processing on the tomographic image;
    the processing circuitry further configured to specify a low sensitivity component from the first shape data, the low sensitivity component being a symmetric component of the first shape data, and to obtain second shape data representing shape of the tissue based on the specified low sensitivity component; and
    the processing circuitry further configured to calculate a refractive power of a peripheral region of a region including a fovea of the subject's eye based, in part, on the second shape data acquired by the processing circuitry.

2. The ophthalmologic information processing apparatus of claim 1, wherein
the processing circuitry specifies, as the low sensitivity component, a symmetric component of the position of the optical system with respect to the subject's eye, with reference to an alignment reference position of the optical system with respect to the subject's eye.

3. The ophthalmologic information processing apparatus of claim 2, wherein
the processing circuitry specifies, as the low sensitivity component, an even order component of the position of the optical system among a polynomial obtained by performing polynomial approximation on the first shape data.

4. The ophthalmologic information processing apparatus of claim 1, wherein
the low sensitivity component includes a component representing a curvature of the tissue.

5. The ophthalmologic information processing apparatus of claim 1, wherein
the processing circuitry specifies, as the low sensitivity component, a component representing a position of a circle, which is obtained by performing circle fitting processing on the first shape data, and a component representing a size of the circle.

6. The ophthalmologic information processing apparatus of claim 1, wherein
the tissue includes a predetermined layer region in a fundus.

7. The ophthalmologic information processing apparatus of claim 6, wherein
the processing circuitry further configured to calculate the refractive power of the peripheral region of the region including the fovea of the subject's eye based on a refractive power obtained by objectively measuring the subject's eye and a parameter representing optical characteristics of the subject's eye corresponding to the shape of the tissue on the basis of the second shape data acquired by the processing circuitry.

8. The ophthalmologic information processing apparatus of claim 7, wherein
the shape of the tissue includes a tilt angle of the tissue with respect to a predetermined reference direction.

9. An ophthalmologic apparatus comprising:
the optical system;
a movement mechanism that moves the subject's eye and the optical system relative to each other; and
the ophthalmologic information processing apparatus of claim 1.

10. The ophthalmologic information processing apparatus of claim 1, wherein the acquisition unit includes one of an optical coherence tomography scanner, an interface circuit, and a recording medium.

11. An ophthalmologic information processing method comprising:
acquiring a tomographic image of a subject's eye formed based on scan data acquired using an optical system for performing optical coherence tomography on the subject's eye;
acquiring first shape data representing shape of a tissue of the subject's eye by performing segmentation processing on the tomographic image; and
specifying a low sensitivity component from the first shape data, the low sensitivity component being a symmetric component of the first shape data, and obtaining second shape data representing shape of the tissue based on the specified low sensitivity component; and
calculating a refractive power of a peripheral region of a region including a fovea of the subject's eye based, in part, on the obtained second shape data.

12. The ophthalmologic information processing method of claim 11, further comprising
calculating the refractive power of the peripheral region of the region including the fovea of the subject's eye based on a refractive power obtained by objectively measuring the subject's eye and a parameter representing optical characteristics of the subject's eye corresponding to the shape of the tissue on the basis of the second shape data acquired in the specifying.

13. An ophthalmologic information processing apparatus comprising:
an acquisition unit configured to acquire a tomographic image of a subject's eye formed based on scan data acquired using an optical system for performing optical coherence tomography on the subject's eye;
processing circuitry configured to acquire first shape data representing shape of a tissue of the subject's eye by performing segmentation processing on the tomographic image; and
the processing circuitry further configured to specify a high sensitivity component from the first shape data, the high sensitivity component being an asymmetric component of the first shape data, and to obtain second shape data representing shape of the tissue by removing the specified high sensitivity component from the first shape data.

14. The ophthalmologic information processing apparatus of claim 13, wherein
the processing circuitry specifies, as the high sensitivity component, an asymmetric component of the position of the optical system with respect to the subject's eye, with reference to an alignment reference position of the optical system with respect to the subject's eye.

15. The ophthalmologic information processing apparatus of claim 14, wherein
the processing circuitry specifies, as the high sensitivity component, an odd order component of the position of the optical system among a polynomial obtained by performing polynomial approximation on the first shape data.

16. The ophthalmologic information processing apparatus of claim 13, wherein
the high sensitivity component includes a component representing an inclination of the tissue with respect to a predetermined reference direction.

17. The ophthalmologic information processing apparatus of claim 13, wherein
the tissue includes a predetermined layer region in a fundus.

18. The ophthalmologic information processing apparatus of claim 17, wherein
the processing circuitry further configured to calculate a refractive power of a peripheral region of a region including a fovea of the subject's eye based on a refractive power obtained by objectively measuring the subject's eye and parameter representing optical characteristics of the subject's eye corresponding to the shape of the tissue on the basis of the second shape data acquired by the processing circuitry.

19. An ophthalmologic apparatus comprising:
the optical system;
a movement mechanism that moves the subject's eye and the optical system relative to each other; and
the ophthalmologic information processing apparatus of claim 13.

20. The ophthalmologic information processing apparatus of claim 13, wherein the acquisition unit includes one of an optical coherence tomography scanner, an interface circuit, and a recording medium.

21. An ophthalmologic information processing method comprising:
acquiring a tomographic image of a subject's eye formed based on scan data acquired using an optical system for performing optical coherence tomography on the subject's eye;
acquiring first shape data representing shape of a tissue of the subject's eye by performing segmentation processing on the tomographic image; and
specifying a high sensitivity component from the first shape data, the high sensitivity component being an asymmetric component of the first shape data, and obtaining second shape data representing shape of the tissue by removing the specified high sensitivity component from the first shape data.

22. The ophthalmologic information processing method of claim 21, further comprising
calculating a refractive power of a peripheral region of a region including a fovea of the subject's eye based on a refractive power obtained by objectively measuring the subject's eye and parameter representing optical characteristics of the subject's eye corresponding to the shape of the tissue on the basis of the second shape data acquired in the specifying.

* * * * *